(12) United States Patent
Kikuchi et al.

(10) Patent No.: US 9,968,583 B2
(45) Date of Patent: May 15, 2018

(54) METHOD OF MANUFACTURE OF LIPOSOME COMPOSITION

(75) Inventors: Hiroshi Kikuchi, Tsukuba (JP); Kenji Hyodo, Tsukuba (JP); Hiroshi Ishihara, Tsukuba (JP)

(73) Assignee: EISAI R & D MANAGEMENT CO., LTD., Tokyo (JP)

( * ) Notice: Subject to any disclaimer, the term of this patent is extended or adjusted under 35 U.S.C. 154(b) by 82 days.

(21) Appl. No.: 13/260,864

(22) PCT Filed: Mar. 30, 2010

(86) PCT No.: PCT/JP2010/055769
§ 371 (c)(1),
(2), (4) Date: Dec. 2, 2011

(87) PCT Pub. No.: WO2010/113983
PCT Pub. Date: Oct. 7, 2010

(65) Prior Publication Data
US 2012/0128757 A1    May 24, 2012

Related U.S. Application Data

(60) Provisional application No. 61/164,653, filed on Mar. 30, 2009, provisional application No. 61/164,678, filed on Mar. 30, 2009.

(30) Foreign Application Priority Data

Mar. 30, 2009  (JP) .................................. 2009-082516
Mar. 30, 2009  (JP) .................................. 2009-082521

(51) Int. Cl.
*A61K 9/127*  (2006.01)
*A61K 31/724*  (2006.01)
(Continued)

(52) U.S. Cl.
CPC .......... *A61K 31/337* (2013.01); *A61K 9/1271* (2013.01); *A61K 9/1278* (2013.01); *A61K 31/704* (2013.01); *A61K 31/7048* (2013.01)

(58) Field of Classification Search
CPC ..... A61K 9/127; A61K 9/1271; A61K 9/1272
(Continued)

(56) References Cited

U.S. PATENT DOCUMENTS 5,192,549 A    3/1993   Barenolz et al.
5,316,771 A    5/1994   Barenholz et al.
(Continued)

FOREIGN PATENT DOCUMENTS

CA    2673924       7/2008
EP    1332755 A1    8/2003
(Continued)

OTHER PUBLICATIONS

Yu, Y et al., "Characterization of the pharmacokinetics of a liposomal formulation of eribulin mesylate (E7389) in mice," Int. J. Pharmaceutics 443:9-16 (Feb. 2013), Elsevier, Amsterdam, Netherlands.
(Continued)

*Primary Examiner* — Gollamudi Kishore
(74) *Attorney, Agent, or Firm* — Sterne, Kessler, Goldstein & Fox P.L.L.C.

(57) ABSTRACT

The present invention provides a method of manufacture of a liposome composition including a step in which: a liposome dispersion liquid containing a liposome, and further containing cyclodextrin in the liposome internal phase is provided and a step in which an active compound is introduced into said liposome internal phase, and the liposome composition.

4 Claims, 5 Drawing Sheets

(51) Int. Cl.
| | |
|---|---|
| A61K 31/337 | (2006.01) |
| A61K 31/704 | (2006.01) |
| A61K 31/7048 | (2006.01) |

(58) Field of Classification Search
USPC .......................................................... 424/450
See application file for complete search history.

(56) References Cited

U.S. PATENT DOCUMENTS

| | | | |
|---|---|---|---|
| 5,571,534 A | 11/1996 | Jalonen et al. | |
| 5,736,155 A | 4/1998 | Bally et al. | |
| 5,759,573 A * | 6/1998 | Kim .............................. | 424/450 |
| 5,821,349 A | 10/1998 | Djedaini-Pilard et al. | |
| 6,051,251 A | 4/2000 | Zalipsky et al. | |
| 6,214,865 B1 | 4/2001 | Littlefield et al. | |
| 6,747,011 B1 | 6/2004 | Zhang | |
| 2005/0118249 A1* | 6/2005 | Webb et al. .................. | 424/450 |
| 2005/0118250 A1 | 6/2005 | Tardi et al. | |
| 2006/0008909 A1* | 1/2006 | Cullis et al. ................. | 435/458 |
| 2006/0147511 A1* | 7/2006 | Panzner et al. ............... | 424/450 |
| 2007/0112176 A1 | 5/2007 | Seiki et al. | |
| 2007/0116753 A1* | 5/2007 | Hong et al. ................... | 424/450 |
| 2007/0155696 A1* | 7/2007 | Ishihara et al. ................ | 514/58 |
| 2009/0196913 A1* | 8/2009 | Huang et al. .................. | 424/450 |
| 2009/0196918 A1* | 8/2009 | Joguparthi et al. ........... | 424/450 |
| 2010/0247629 A1 | 9/2010 | Gabizon | |
| 2011/0262524 A1 | 10/2011 | Bally et al. | |
| 2012/0058178 A1 | 3/2012 | Kikuchi et al. | |
| 2014/0044777 A1 | 2/2014 | Kikuchi et al. | |

FOREIGN PATENT DOCUMENTS

| | | |
|---|---|---|
| EP | 1921086 A1 | 5/2008 |
| EP | 2123260 A1 | 11/2009 |
| EP | 2415464 A1 | 2/2012 |
| JP | 7-501813 A | 2/1995 |
| JP | 8-509230 A | 10/1996 |
| JP | 2004-516247 A | 6/2004 |
| JP | 2005-50900 A | 4/2005 |
| JP | 2005-509000 A | 4/2005 |
| JP | 2006-513189 A | 4/2006 |
| JP | 5551683 B2 | 5/2014 |
| WO | WO 93/11757 A1 | 6/1993 |
| WO | WO 94/23697 A1 | 10/1994 |
| WO | WO 99/65894 A1 | 12/1999 |
| WO | WO 02/032399 A1 | 4/2002 |
| WO | WO 03/041681 A2 | 5/2003 |
| WO | WO 2004/058140 A2 | 7/2004 |
| WO | WO 2005/046643 A2 | 5/2005 |
| WO | WO 2006/037230 A1 | 4/2006 |
| WO | WO 2007/026869 A1 | 3/2007 |
| WO | WO 2008/080367 A1 | 7/2008 |
| WO | WO2010/113984 A1 | 10/2010 |

OTHER PUBLICATIONS

Response filed Jan. 21, 2013, to the Peruvian Opposition dated Nov. 23, 2012, for Peruvian Patent Application No. 001735-2011/DIN.
Response filed Dec. 27, 2012, to the Taiwan office action dated Jun. 22, 2012 for TW Patent Appl. No. 099109838.
Package insert for "Halaven®, 1 mg," Jul. 2011, Eisai Co., Ltd., Tokyo, Japan.
Package Insert for "Novantron® Injection 10mg, 20mg," Nov. 2011, ASKA Pharmaceutical Co., Ltd., Tokyo, Japan.
"Approval Decision Letter from the Intellectual Property Office" issued Jan. 23, 2013, for TW Patent Appl. No. 099109838, Intellectual Property Office, Ministry of Economic Affairs, R.O.C., Taipei, Taiwan.
"Amendment and Reply under 37 C.F.R. § 1.111," including two exhibits, filed Feb. 1, 2013, for U.S. Appl. No. 13/260,872.
International Search Report (ISR) for PCT/JP2010/055769, I.A. fd: Mar. 30, 2010, dated Jun. 8, 2010 from the Japanese Patent Office, Tokyo, Japan.

International Preliminary Report on Patentability (IPRP), Chapter I of the Patent Cooperation Treaty, including the Written Opinion for PCT/JP2010/055769, I.A. fd: Mar. 30, 2010, dated Nov. 15, 2011, front the International Bureau of WIPO, Geneva, Switzerland.
Arima, H et al, "Enhancement of antitumor effect of doxorubicin by its compiexation with gamma-cyclodextrin in pegylated liposomes," J Drug Target 14(4): 225-232 (May 2006), Informa Healthcare, London, England.
DesJardins, C et al., "A high-performance liquid chromatography-tandem mass spectrometry method for the clinical combination study of carboplatin and anti-tumor agent eribulin mesylate (E7389) in human plasma," J Chromatogr B Analyt Technol Biomed Life Sci; 875(2): 373-382 (Nov. 2008), Elsevier, New York.
Dos Santos, N et al., "pH gradient loading of anthracyclines into cholesterol-free liposomes: enhancing drug loading rates through use of ethanol," Biochim Biophys Acta 1661(1): 47-60 (Feb. 2004), Elsevier, Amsterdam, Netherlands.
Fatouros, DG et al., "Liposomes encapsulating prednisolone and prednisolone-cyclodextrin complexes: comparison of membrane integrity and drug release," Eur J Pharm Sci 13(3): 287-296 (Jun. 2001), Elsevier. Amsterdam, Netherlands.
Hagiwara, Y et al. "Preparation and pharmaceutical evaluation of liposomes entrapping salicylic acid/gamma-cyclodextrin conjugate," Chem Pharm Bull (Tokyo) 54(1): 26-32 (Jan. 2006), Pharmaceutical Society of Japan. Tokyo, Japan.
Jordan, MA et al., "The primary antimitotic mechanism of action of the synthetic halichondrin E7389 is suppression of microtubule growth," Mol Cancer Ther 4: 1086-1095 (Jul. 2005), Am. Assoc Cancer Research, Philadelphia, PA.
Maestrelli, F et at, "Effect of preparation technique on the properties of liposomes encapsulating ketoprofen-cyclodextrin complexes aimed for transdermal delivery," Int J Pharm 312(1-2): 53-60 (Apr. 2006), Elsevier, Amsterdam, Netherlands.
Mayer, LD et al., "Uptake of adriamycin into large unilamellar vesicles in response to a pH gradient," Biochim Biophys Acta, 857(1): 123-126 (May 1986), Elsevier, Amsterdam, Netherlands.
Matsumura, Y et al., "A New Concept for Macromolecular Therapeutics in Cancer Chemotherapy: Mechanism of Tumoritropic Accumulation of Proteins and the Antitumor Agent Smancs," Cancer Res 46: 6387-6392 (Dec. 1986), Am. Assoc. Cancer Research, Baltimore, MD.
Okouneva, T et al., "Inhibition of centromere dynamics by eribulin (E7389) during mitotic metaphase," Mol Cancer Ther 7: 2003-2011 (Jul. 2008), Am. Assoc Cancer Research, Philadelphia, PA.
Piel, G et al., "Betamethasone-in-cyclodextrin-in-liposome: the effect of cyclodextrins on encapsulation efficiency and release kinetics," Int J Pharm P312(1-2): 75-82 (Apr. 2006), Elsevier, Amsterdam, Netherlands.
Wang, Y, "Eribulin mesilate—Antimitotic drug tubulin polymerization inhibitor oncolytic," Drugs of the Future 32(8): 681-698 (Aug. 2007), Thomson Reuters, New York.
International Preliminary Report on Patentability (IPRP), Chapter I of the Patent Cooperation Treaty, including the Written Opinion for PCT/JP2010/055770, I.A. fd: Mar. 30, 2010, dated Nov. 15, 2011, from the International Bureau of WIPO, Geneva, Switzerland.
Response filed Feb. 28, 2013, to the Korean office action dated Dec. 28, 2012 for KR Patent Appl. No. 10-2011-7022860.
Package insert, including a translation of the header and sections entitled: "Storage," "Expiration date," "Structural formula" and "Physiochemical properties," for Halaven® Intravenous Injection 1 mg, (Eribulin mesylate preparation), Jul. 2011, $2^{nd}$ edition, Eisai Co., Ltd., Tokyo, Japan.
Header and sections III.1.(2) "Solubility"; (5) "Acid/Base Dissociation Constant" and (6) "Partition Coefficient" of the Pharmaceutical Interview Form (IF) for Halaven® Intravenous Injection 1 mg, (Eribulin mesylate preparation), Jul. 2011 ($2^{nd}$ Edition, Eisai Co., Ltd., Tokyo, Japan.
Pharmaceutical Interview Form (IF) for Halaven® Intravenous injection, 1 mg, (Eribulin mesylate preparation), Jul. 2011, ($2^{nd}$ Edition) Eisai Co., Ltd., Tokyo, Japan.
Package insert, including a translation of the header and sections entitled: "Storage," "Expiration date," Precautions, Structural formula, and "Properties," for Novantron® Injection 10mg,

(56) References Cited

OTHER PUBLICATIONS

"Novantron® Injection 20mg," (Mitoxantrone hydrochloride injection), Nov. 2011, ASKA Pharmaceutical Co., Ltd., Tokyo, Japan.
Sections III.1.(2), (5) and (6) of the Pharmaceutical Interview Form (IF) for Pharmaceutical Interview Form (IF) for Adriacin® Injection 10 and for Adriacin® Injection 50, (Doxorubicin hydrochloride for injection), Aug. 2011, (16$^{nd}$ Edition), Kyowa Hakko Kirin Co., Ltd., Japan.
Pharmaceutical Interview Form (IF) for Adriacin® Injection 10 and for Adriacin® Injection 50, (Doxorubicin hydrochloride for injection), Aug. 2011, (16$^{nd}$ Edition), Kyowa Hakko Kirin Co., Ltd., Japan.
Applicant's "Observations" filed Apr. 2, 2013, in response to the first Chinese office action for CN Patent Appl. No. 201080014698.2.
"Oncovin® for injection 1 mg—Vincristine Sulfate Preparation," Package Insert, including a translation of the header and sections entitled: "Structural formula" and "Properties," Nippon Kayaku Co., Ltd., revision of Aug. 2009.
"Rozeus® Intravenous Solution 10 mg—Rozeus® Intravenous Solution 40 mg—Vinorelbine Ditartrate Intravenous Solution," Package Insert, including a translation of the header and sections entitled: "Structural formula" and "Properties," Nippon Kayaku Co., Ltd., revision of Nov. 2009.
"Exal® for Injection 10 mg—Japanese Pharmacopeia (JP) Vinblastine Sulfate for Injection," including a translation of the header and sections entitled: "Structural formula" and "Properties," Nippon Kayaku Co.,Ltd., Package Insert, revision of Jul. 2011.
"Adriacin® Injection 10—Adriacin® Injection 50," Package Insert, including a translation of the header and sections entitled: "Structural formula" and "Solubility," revision of Aug. 2011.
"Preliminary Conclusion (on non-Patentability)" for UA Patent Application No. a201111426, State Service of Intellectual Property of Ukraine, dated Apr. 8, 2013.
"Substantive Examination Adverse Report (Section 30(1)/30(2))," for Malaysian Patent Application No. PI 201 1004382, dated Apr. 15, 2013, Intellectual Property Corporation of Malaysia, Kuala Lumpar, Malaysia.
Final Office Action for U.S. Appl. No. 13/260,872, dated Apr. 24, 2013, The United States Patent and Trademark Office, Alexandria, VA.
Applicant's response filed May 3, 2013 to the Communication Pursuant to Rules 70(2) and 70a(2) EPC dated Oct. 25, 2012 for EP Application No. 10 758 754.5.
Applicant's response filed May 29, 2013, to the Communication Pursuant to Rules 70(2) and 70a(2) EPC dated Nov. 19, 2012 for EP Application No. 10 758 755.2.
Response filed Jun. 19, 2013, to the Office Action dated Dec. 19, 2012, for Canadian patent application No. 2,756,811, by Applicant Eisai R&D Management Co., Ltd., in the Canadian Intellectual Property Office, Gatineau, Québec, Canada.
Requisition by the Examiner in Accordance with Subsection 30(2) of the Patent Rules, dated Jul. 17, 2013, for Canadian patent application No. 2,756,811, the Canadian Intellectual Property Office, Gatineau, Québec, Canada.
Response filed Jun. 14, 2013, to the Substantive Examination Adverse Report dated Apr. 15, 2013, for Malaysian patent application No. PI 2011004382, by Applicant Eisai R&D Management Co., Ltd., in the Intellectual Property Corporation of Malaysia, Kuala Lumpur, Malaysia.
2$^{nd}$ Office action—Subject Matter: Communication Regarding Novelty Examination, dated Apr. 22, 2013, for Mexican patent application No. MX/a/2011/009632, Mexican Institute of Industrial Property, Mexico.
Response on Preliminary Conclusion on Non-patentability, filed Jun. 11, 2013, for Ukrainian patent application No. a201111426, in the Ukrainian Institute of Industrial Property, Kyiv, Ukraine.
Notice of Allowance, dated Jul. 23, 2013, for Ukrainian patent application No. a201111426, the Ukrainian Institute of Industrial Property, Kyiv, Ukraine.

Notice of Preliminary Rejection, dated Jul. 22, 2013, for Korean patent application No. 10-2011-7022860, the Korean Intellectual Property Office, Daejeon, Republic of Korea.
Examiner's Report Issued on Patent of Invention Application, dated Jul. 11, 2013, for Chilian patent application No. 2444-2011, National Institute of Industrial Property, Santiago, Chili.
Substantive Examination Report, dated Aug. 8, 2013, for Philippines patent application No. 1/2011/501838, Intellectual Property Office of the Philippines, Taguig City, Philippines.
Office action dated Aug. 8, 2013, for Colombian patent application No. 11-130828, Superintendent of Industry and Trade, Bogotá, Columbia.
Notification on the Result of Substantive Examination, for Vietnamese patent application No. 1-2011-02950, dated Aug. 16, 2013, National Office of Intellectual Property, Hanoi, VietNam.
Notification of the Second Office Action, dated Aug. 8, 2013, for Chinese patent application No. 201080014698.2, The State Intellectual Property Office of the People's Republic of China, Beijing, China.
Peleg-Shulman, T et al., "Characterizatio of sterically stabilized cisplatin liposomes by nuclear magnetic resonance," Biochim Biophys Acta, Feb. 2001; 1510(1-2): 278-291, Elsevier, Amsterdam, Netherlands.
Opposition to Peruvian patent application No. 001735-2011/DIN, by Farmindustria S.A., dated Nov. 23, 2012, National Institute for the Defense of Competition and Protection of Intellectual Property (INDECOPI), Lima, Peru.
Canadian Office Action regarding Canadian Patent Application No. 2,756,811, dated Dec. 19, 2012, Canadian Intellectual Property Office, Toronto, Ontario, Canada.
Eisai R&D Management Co., Ltd. Response, filed Jan. 14, 2013, to the Columbian Opposition dated Jul. 25, 2012, for Columbian Application No. 11-130828.
Examiner's first report for AU patent application No. 2010232347, dated May 11, 2012, IP Australia, Woden, Australia.
Examiner's report for Taiwan patent application No. 099109838, dated Jun. 22, 2012, Taiwan Intellectual Property Office, Taipei, Taiwan.
Non-final Office action for U.S. Appl. No. 13/260,872, dated Aug. 1, 2012, United States Patent and Trademark Office, Alexandria, VA.
Kuznetsov, G. et al., "Antiproliferative effects of halichondrin B analog eribulin mesylate (E7389) against paclitaxel-resistant human cancer cells in vitro," Abstract C58, AACR-NCI-EORTC International Conference: Molecular Targets and Cancer Therapeutics, Oct. 22-26, 2007, San Francisco, CA.
NORMOSOL®-R packaging insert; downloaded from http://whatsthedose.com/spl/0409-7670.html on Jul. 20, 2012, revised Oct. 2006, Hospira, Inc.
Satsuka, Y. Section 2 in "Recent Evolution of Liposome Application—Toward Development of Artificial Cells." pp. 33-37 (2005), N. Oku et al., eds., NTS.
Kikruchi, H. et al., "Liposome I—Method of Preparing and Testing," Cell Engineering 2(9):1136-1149 (1983).
Examiner's report for New Zealand patent application No. 595212, dated Aug. 14, 2012, New Zealand Intellectual Property Office, Wellington, New Zealand.
Kikuchi, H. et al., "Liposome I—Method of Preparing and Testing," Cell Engineering 2(9):1136-1149 (1983).
Office action for Mexican Patent Application No. MX/a/2011/009632, dated Aug. 7, 2012, Instituto Mexicano de la Propiedad Industrial, Mexico.
Extended European search report including the supplementary European search report and the European search opinion, for EP Appl. No. 10758754.5, dated Oct. 8, 2012, European Patent Office, Munich, Germany.
Loftsson, T et al., "Solubilization and stabilization of drugs through cyclodextrin complexation," Acta Pharm. Nord. 3(4):215-217 (Jan. 1991). Elsevier Science Publishers, Amsterdam, NL.
Haran, G et al., "Transmembrane ammonium sulfate gradients in liposomes produce efficient and stable entrapment of amphipathic weak bases," Biochim Biophys Acta 1151(2): 201-215 (Sep. 1993), Elsevier Science Publishers, Amsterdam, NL.

(56) References Cited

OTHER PUBLICATIONS

Extended European search report including the supplementary European search report and the European search opinion, for EP Appl. No. 10758755.2, dated Oct. 12, 2012, European Patent Office, Munich, Germany.
FormuMax Scientific Inc.: "Doxoves—Liposome Doxorubicin compared to Doxil®", Doxoves—Liposomal Doxorubicin, retrieved Sep. 24, 2012, from the internet url: www.liposomeexpert.com/categories/Drug-Loaded-Liposomes.
Bolotin, EM et al., "Ammonium sulfate gradients for efficient and stable remote loading of amphipathic weak bases into liposomes and ligandoliposomes," J. Liposome Res. 4(1): 455-479 (Jan. 1994), Taylor & Francis, Philadelphia, PA.
Extended European search report including the supplementary European search report and the European search opinion, for EP Appl. No. 10758755.2, dated Oct. 31, 2012, European Patent Office, Munich, Germany.
Decision on Grant for Russian patent application No. 2011139715, dated Sep. 25, 2012, Russian Agency for Patent and Trademarks, Moscow, Russia.
Opposition to Colombia patent application No. 11-130828, by Laboratorios Synthesis S.A.S., published Apr. 30, 2012 in the Colombia Industrial Property Gazette No. 643, Superintendence of Industry and Trade, Bogota, Colombia.
Notification of the First Office Action, Chinese patent application No. 201080014698.2, dated Oct. 24, 2012, The State Intellectual Property Office of the People's Republic of China, Beijing, China.
Fude, ed., in "Liposomes," CUI, $5^{th}$ edition, People's Press of Hygiene, Mar. 2004, pp. 386-394, China.
Mexican Response filed on Jan. 7, 2013, to the Mexican Office Action dated Aug. 7, 2012, for Mexican Application No. MX/a/2011/0009632.
Notice of Preliminary Rejection for Korean patent application No. 10-2011-7022860, dated Dec. 28, 2012, Korean Intellectual Property Office, Daejeon, Republic of Korea.
Corrected written opinion for Extended European Search Report, dated Dec. 17, 2012, for European patent application No. 10758755.2, European Patent Office, Munich, Germany.
International Search Report (ISR) for PCT/JP2010/055770, I.A. fd: Mar. 30, 2010, dated Jun. 1, 2010 from the Japanese Patent Office, Tokyo, Japan.
Russian Office action for RU Application No. 2011139715/20(059371), dated Nov. 28, 2011, its partial English translation and Applicant's response filed Jan. 30, 2012.
Notice of Allowance issued by the Superintendence of Industry and Commerce on Jan. 21, 2014 for Colombian application No. 11-130828-00000-0000.
Notice of Reasons for Rejection, issued on Feb. 6, 2014 for Japanese application No. 2011-507240, Japan Patent Office, Tokyo, Japan.
Response filed with the Intellectual Property Office of New Zealand on Feb. 7, 2014 for New Zealand application No. 595212.
Response filed with the Korean Intellectual Property Office on Jan. 22, 2014 for Korean application No. 10-2011-7022860.
Preliminary amendment and Exhibit filed at the USPTO on Oct. 24, 2013 for U.S. Appl. No. 14/061,426.
Communication pursuant to Article 94(3) EPC, issued on Jan. 24, 2014 for European application No. 10 758 755.2, European Patent Office, Munich Germany.
Notice of Allowance regarding Canadian Patent Application No. 2,756,811, dated Feb. 10, 2014, Canadian Intellectual Property Office, Toronto, Ontario, Canada.
Further Examination Report Acceptance for New Zealand patent application No. 595212, dated Feb. 25, 2014, New Zealand Intellectual Property Office, Wellington, New Zealand.
Communication regarding novelty examination for Mexican patent application No. MX/a/2011/009632, dated Jan. 17, 2014, Mexican Institute of Industrial Property, Cuauhtémoc, Distrito Federal, Mexico.

Notice of Reasons for Rejection, issued on Feb. 27, 2014 for Japanese application No. 2011-507239, Japan Patent Office, Tokyo, Japan.
Response filed with the Industrial Property Institute on Mar. 11, 2014 for Chilean application No. 2444-2011.
Response to the Result of Substantive Examination Stage I on Indonesian Patent Application No. W-00 2011 03470 on Mar. 25, 2014.
Decision to Grant a Patent, for Japanese Patent Application No. JP2011-507240, Japanese Patent Office, mailed May 7, 2014.
Notice of Preliminary Rejection, for Korean Patent Application No. 10-2011-7022860, Korean Intellectual Property Office, Daejeon, Republic of Korea, dated May 20, 2014.
Notification of Third Office Action, for Chinese Patent Appl. No. 201080014698.2, dated Mar. 28, 2014, The State Intellectual Property Office of the People's Republic of China, Beijing, China.
Applicants' response filed Apr. 7, 2014, to the February 6, 2014 office action from the Japanese Patent Office issued for Japanese Patent Appl. No. 2011-507240.
Eisai R&D Management Co., Ltd., Argument and Amendment filed Apr. 28, 2014, in reply to the Feb. 25, 2014 (dated Feb. 27, 2014) office action from the Japanese Patent Office issued for Japanese Patent Appl. No. 2011-507239.
Eisai R&D Management Co., Ltd. Response and Amendment filed Jul. 18, 2014, in reply to the Korean office action dated May 20, 2014 for KR Patent Appl. No. 10-2011-7022860.
Eisai R&D Management Co., Ltd. Response filed Jun. 17, 2014, in reply to the Mexican office action (Official Communication No. 4069) for MX Patent Appl. No. MX/a/2011/009632.
Notice of Allowance issued on Aug. 6, 2014 for Chinese Patent Application No. 201080014698.2, The People's Republic of China State Intellectual Property Office, Beijing, China.
Office Action dated Aug. 4, 104 for Israel Patent Appl. No. 215059, Israel Patent Office, Jerusalem, Israel.
Decision to Grant a Patent, for Japanese Patent Application No. JP2014-092382, Japanese Patent Office, Tokyo, Japan, dated Jun. 2, 2015.
Subsequent Substantive Examination Report, for Philippines Patent Appl. No. 1/2011/501838, dated Jun. 4, 2015, The Intellectual Property Office of the Philippines, Taguig City, Philippines.
Restriction requirement for U.S. Appl. No. 14/061,426, dated May 15, 2015, from the USPTO, Alexandria, VA.
Preliminary amendment for Japanese Patent Application No. 2014-092382, filed with the Japanese Patent Office, Tokyo, Japan, dated May 28, 2014 by the applicant, Eisai R&D Management Co., Ltd.
Amendment and argument in reply to the office action dated Jan. 28, 2015, for Japanese Patent Application No. 2014-092382, filed with the Japanese Patent Office, Tokyo, Japan, on Mar. 27, 2015 by the applicant, Eisai R&D Management Co., Ltd.
Subsequent Substantive Examination Report, dated Sep. 17, 2014, for Philippines patent application No. 1/2011/501838, Intellectual Property Office of the Philippines, Taguig City, Philippines.
Notice of Final Rejection for Korean Patent Application No. 10-2011-7022860, Korean Intellectual Property Office, Daejeon, Republic of Korea, dated Sep. 23, 2014.
Office Action dated Sep. 29, 2014 for Peruvian application No. 001735-2011/DIN, INDECOPI, Lima, Peru.
Eisai R&D Management Co., Ltd. Response filed with INDECOPI dated Oct. 27, 2014, in reply to the Sep. 29, 2014 office action for Peruvian Patent Appl. No. 001735-2011/DIN.
Applicant Eisai R&D Management Co., Ltd.'s Response filed Nov. 11, 2014, submitting English translation of JP 5551683 B2, in reply to Paper No. 9 dated Sep. 17, 2014, for Philippine patent application No. 1-2011-501838, filed with the Intellectual Property Office of the Philippines, Taguig City, Philippines.
Applicant Eisai R&D Management Co., Ltd. "Memorandum in Response to Official Action dated Aug. 4, 2014," filed with the Israel Patent Office on Dec. 2, 2014, for Israel Patent Application No. 215059.
Eisai R&D Management Co., Ltd. Response filed Dec. 24, 2014, in reply to the Notice of Final Rejection dated Sep. 23, 2014, for KR Patent Appl. No. 10-2011-7022860.

(56) References Cited

OTHER PUBLICATIONS

Notice of Allowance dated Jan. 9, 2015 for KR Patent Appl. No. 10-2011-7022860, Korean Intellectual Property Office, Daejeon, Republic of Korea.
Opposition filed against Peru Patent Appl. No. 001735-2011/DIN by Farmindustria S.A. de Perú, dated Jan. 20, 2015.
Petition of Eisai R&D Management Co., Ltd., for Japanese Patent Application No. 2014-092382, filed with the Japanese Patent Office, Tokyo, Japan, on Dec. 26, 2014.
Notice of Reasons for Rejection, for Japanese Patent Application No. 2014-092382, dated Jan. 28, 2015, by the Japanese Patent Office, Tokyo, Japan.
Examiner's Report Issued on Patent of Invention Application for Chilean Patent Application No. 2444-2011, by the National Institute of Industrial Property, Santiago, Chili, dated Jan. 21, 2015.
Kim, S. et al., "Multivesicular liposomes containing cytarabine entrapped in the presence of hydrochloric acid for intracavitary chemotherapy," Cancer Treatment Reports 71:705-711, Jul./Aug. 1987, National Cancer Institute, Silver Spring, MD.
Kim, S. et al., "Preparation of Multivesicular liposomes," Biochim. Biophys. Acta 728:339-348 (1983), Elsevier Biomedical Press, Amsterdam, Netherlands.
"Decision to Grant a Patent," dated Aug. 27, 2014, for Japanese Patent Appl. No. 2011-507239, the Japanese Patent Office, Tokyo, Japan.
Eisai &D Management Co., Ltd. Response filed Apr. 16, 2015 to the Jan. 21, 2015 office action, for Chilean application No. 2444-2011, filed at the National Institute of Industrial Property, Santiago, Chili.
Eisai R&D Management Co., Ltd. Supplemental Response filed on Jun. 5, 2015 for Chilean application No. 2444-2011, filed at the National Institute of Industrial Property, Santiago, Chili.
Eisai R&D Management Co., Ltd. amendment (filed May 20, 2015) and argument (filed May 21, 2015) with INDECOPI, for Peruvian application No. 001735-2011/DIN.
Notification: Resolution N°000089-2015/CIN-INDECOPI issued Jul. 16, 2015, for Peruvian patent appl. No. 001735-2011 DIN, by the National Institute for the Defense of Competition and Protection of Intellectual Property (INDECOPI), Lima, Peru.
Applicant Eisai R&D Management Co., Ltd.'s Response filed Jul. 24, 2015 for Philippines patent application No. 1/2011/501838, Intellectual Property Office of the Philippines, Taguig City, Philippines.
Reply to Restriction Requirement, filed Jul. 15, 2015, for U.S. Appl. No. 14/061,426, at the United States Patent and Trademark Office, Alexandria, VA.
Patent Examination Report No. 1, for AU patent application No. 2014200717, dated Aug. 14, 2015, by IP Australia, Woden ACT, Australia.
Completion of Final Requirements, dated Aug. 27, 2015 by the Intellectual Property Office of the Philippines, for Philippines patent application No. 1/2011/501838, Taguig City, Philippines.
Non-final Office action dated Sep. 24, 2015, for U.S. Patent Appl. No. 14/061,426 (Kikuchi et al.), by the United States Patent and Trademark Office, Alexandria, VA.
Eisai R&D Management Co., Ltd. Appeal filed Aug. 12, 2015, with INDECOPI, for Peruvian application No. 001735-2011/DIN.
Eisai R&D Management Co., Ltd.'s Response filed Sep. 18, 2015, to the Aug. 27, 2015 office action for Philippines patent application No. 1-2011-501838.
Eisai R&D Management Co., Ltd. response filed Apr. 18, 2016, to "Technical Report on the Application No. PCT 1637/2011," filed at the Egyptian Patent Office, Cairo, Egypt, for Egyptian Patent Appl. No. PCT 1637/2011.
Communication under Rule 71(3) EPC: Intention to grant, for EP patent application No. EP 10 758 755.2, dated Feb. 25, 2016, The European Patent Office, Munich, Germany.
Amendment and reply including Exhibit 1—filed Dec. 22, 2015 for U.S. Appl. No. 14/061,426, filed at the United States Patent and Trademark Office, Alexandria, VA.

Final Office action dated Mar. 18, 2016, for U.S. Appl. No. 14/061,426 (Kikuchi et al.), by the United States Patent and Trademark Office, Alexandria, VA.
Maurer-Spurej, E et al., "Factors influencing uptake and retention of amino-containing drugs in large unilamellar vesicles exhibiting transmembrane pH gradients," Biochim Biophys Acta. Jan. 12, 1999;1416(1-2):1-10, Elsevier, Netherlands.
"Ammonium cation," from The Illustrated Glossary of Organic Chemistry, one page, downloaded on Mar. 9, 2016 from http://www.chem.ucla.edu/harding/IGOC/A/ammonium_cation.html, Steven A. Hardinger, UCLA.
Onium Compounds: IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic et al., updates compiled by A. Jenkins. url for Onium entry: http://goldbook.iupac.org/O04291.html, two pages, last updated Feb. 24, 2014; version: 2.3.3., doi:10.1351/goldbook. O04291, downloaded on Mar. 9, 2016.
Transmittal letter and office action entitled "Technical Report on the Application No. PCT 1637/2011," from The Egyptian Patent Office, dated Jan. 14, 2016, for Egyptian Patent Appl. No. PCT 1637/2011, Cairo, Egypt.
Notice of Acceptance for AU Patent Appl. No. 2014200717 dated Feb. 13, 2016, IP Australia.
Office action for Vietnamese Patent Appl. No. 1-2011-02950, dated Mar. 31, 2016, Ministry of Science & Technology, Vietnam.
Eisai R&D Management Co., Ltd. response filed Mar. 14, 2016 to the office action dated Dec. 11, 2015, for Chilean Patent Appl. No. 2444-2011.
Drummond, D.C. et al., "Optimizing Liposomes for Delivery of Chemotherapy Agents to Solid Tumors," Pharmacological Reviews 51(4):691-743 (1999), The American Society for Pharmacology and Experimental Therapeutics, United States.
Notice of the Result of Substantive Examination Pursuant to Article 52 (1) of Patent Law No. 14/2001, dated Nov. 29, 2013 for Indonesian application No. W-00 2011 03470, Ministry of Law and Human Rights of the Republic of Indonesia, Tangerang, Indonesia.
Response filed with the Mexican Institute of Industrial Property on Sep. 18, 2013 for Mexican application No. MX/a/2011/009632.
Response filed with the Canadian Intellectual Property Office dated Jan. 16, 2014 for Canadian application No. 2,756,811.
Opposition filed on Jan. 16, 2014 against Chilean application No. 2444-2011.
Response to the Notification of the Result of Substantive Examination filed with the National Office of Intellectual Property, dated Dec. 13, 2013 for Vietnamese application No. 1-2011-02950.
Office Action dated Jan. 9, 2014 for Peruvian application No. 001735-2011/DIN, INDECOPI, Lima, Peru.
Response filed with the Trade and Industry Superintendence on Dec. 2, 2013 for Colombian application No. 11-130828-00010-000.
Response filed with INDECOPI, on Jan. 20, 2014 for Peruvian application No. 001735-2011/DIN.
Response, "Observations (OA2)" filed with the State Intellectual Property Office of the Peoples' Republic of China (SSIPO) on Dec. 23, 2013 for Chinese application No. 201080014698.2.
Communication pursuant to Article 94(3) EPC, dated Jan. 24, 2014 for European application No. 10 758 754.5, European Patent Office, Munich Germany.
"Filed Notice of Opposition" for Peruvian Patent Application No. 001798-2015, dated Jan. 25, 2016, National Institute for the Defense of Competition and Protection of Intellectual Property (INDECOPI), Lima, Peru.
"Residues—definition of Residues by Medical dictionary," downloaded from www.freedictionary.com on Jul. 15, 2014, Farlex, Inc, source url: http://medical-dictionary.thefreedictionary.com/Residues.
Cullis, PR et al., "pH gradients and membrane transport in liposomal systems," Trends in Biotechnology, 1991, 9(8): 268-272, Elsevier Science Publishers Ltd., Barking, UK.
Eisai "Material Safety Data Sheet," Product Name: Eribulin Mesylate Injection; Drug Substance Name: Eribulin Mesylate, 6 pages, first issue Oct. 28, 2009, prepared by Greg Baker.

(56) References Cited

OTHER PUBLICATIONS

Eisai R&D Management Co., Ltd. response filed Dec. 22, 2015, with IP Australia, for Australian patent application No. 2014200717.
Notice before Allowance of Israel Patent Application No. 215059, dated Nov. 25, 2015, The Israel Patent Office.
Supreme Resolution regarding Peruvian Patent Application No. 001735-2011DIN, Applicant: Eisai R&D Management Co., Ltd.; Opponent: Farmindustria S.A., dated Nov. 30, 2015, INDECOPI, Lima, Peru.
Examiner's Report Issued on Patent of Invention Patent Application, dated Dec. 18, 2015 for Chilean patent application No. 2444-2011, National Institute of Industrial Property, Santiago, Chili.
Voluntary amendment filed Jul. 7, 2016 for Cambodian Patent Application No. KH/P/10/00097.
Transmittal letter and office action entitled "Technical Report on the Application No. PCT 1637/2011," issued by The Egyptian Patent Office, dated Jan. 3, 2017, for Egyptian Patent Appl. No. PCT 1637/2011, Cairo, Egypt.
Examination report under sections 12 & 13 of the Patents Act, 1970 and the Patents Rules, 2003, for Indian Patent Application No. 6850/DELNP/2011, dated Nov. 10, 2016, The Patent Office, Intellectual Property India.
Communication under Rule 71(3) EPC: Intent to grant, for European Patent Application No. 10 758 754.5, dated Jan. 19, 2017, European Patent Office, Munich Germany.
Excerpted file history of U.S. Appl. No. 14/061,426: RCE, ADS and Amendment and Reply filed Sep. 19, 2016, filed at the United States Patent and Trademark Office, Alexandria, VA.
Final rejection for Algerian Patent Appl. No. 110640, dated Aug. 18, 2013, by the Institut National Algérien de la Propriété Industrielle, partial translation.
Eisai R&D Management Co., Ltd., response filed Aug. 29, 2016, in reply to the office action for Algerian Patent Appl. No. 110640, partial translation.
Substantive Examination Clear Report—Section 30(1)/30(2) for Malaysian Patent Appl. No. PI 2011004382, dated Sep. 30, 2016, by the Intellectual Property Corporation of Malaysia.
Eisai R&D Management Co., Ltd Response filed on May 30, 3016 to the Mar. 31, 2016 Vietnamese office action for Vietnamese Patent Appl. No. 1-2011-02950.
Eisai R&D Management Ltd. Response to Opposition, response filed Apr. 28, 2016 for Peruvian Patent Appl. No. 1798-2015.
Official notice: Intention to grant patent and invitation to pay fees for grant for Vietnamese patent application No. 1-2011-02950, dated Jan. 24, 2017, National Office of Intellectual Property, Hanoi, Vietnam.
Eisai R&D Management Co., Ltd. Response filed Mar. 30, 2017 at the Egyptian Patent Office, Cairo, Egypt, against the Office Decision dated Jan. 3, 2017, for Egyptian Patent Application No. PCT 1637/2011.
Notice of Allowance dated Apr. 20, 2017, for Indonesian Patent Appl. No. W00201103470, Department of Justice and Human Right of the Republic of Indonesia, Jakarta, Indonesia.
Excerpted file history, U.S. Appl. No. 14/061,426, Non-final rejection dated May 31, 2017.
Hearing Notice in Reference of Indian Application No 6850/DELNP/2011, dispatched Aug. 17, 2017, from The Patent Office, Intellectual Property india.
Response and Amendment to Result for Hearing Notice, filed Oct. 3, 2017, for Indian Patent Application No. 6850/DELNP/2011, with Intellectual Property India listing dated Mar. 10, 2017 showing entry number for Form 30 for Indian Patent Application No. 6850/DELNP/2011.
Excerpted file history U.S. Appl. No. 14/061,426 (Kikuchi et al.): final Office action dated Oct. 30, 2017 by the United States Patent and Trademark Office, Alexandria, VA.
Excerpted file history, U.S. Appl. No. 14/061,426, Amendment and Reply filed Aug. 30, 2017 at the United States Patent and Trademark Office, Alexandria, VA.
Response filed Sep. 30, 2013, to Paper No. 7 dated Aug. 8, 2013, for Philippine patent application No. 1-2011-501838, by Applicant Eisai R&D Management Co., Ltd., in the Intellectual Property Office of the Philippines, Taguig City, Philippines.

* cited by examiner

[Fig. 1]
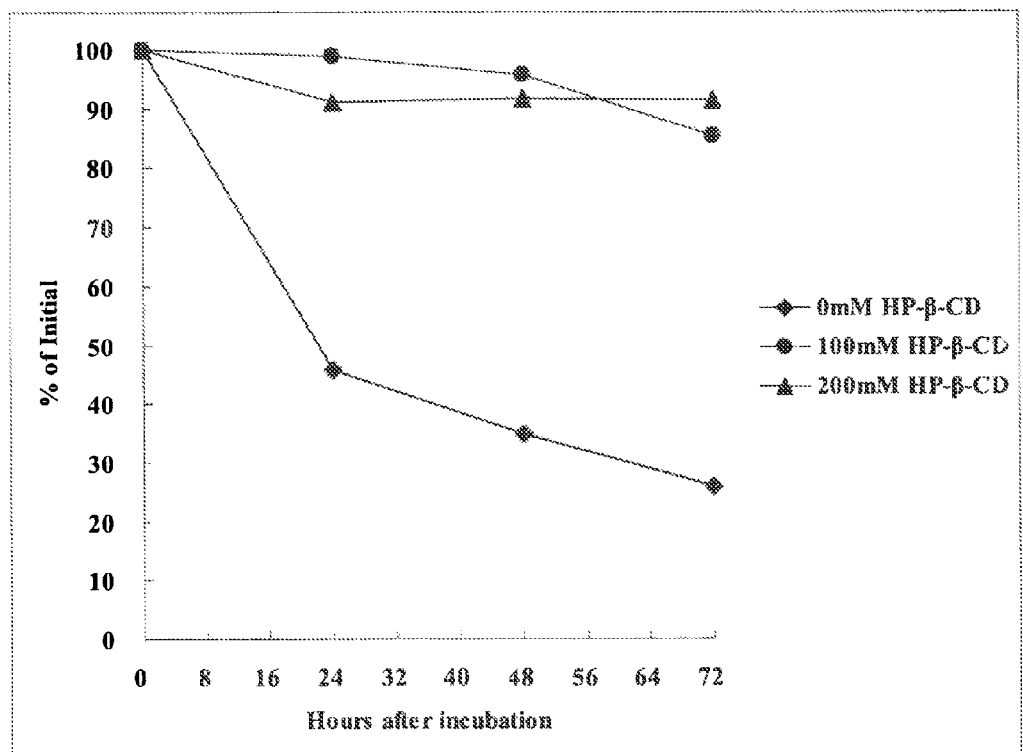

[Fig. 2]
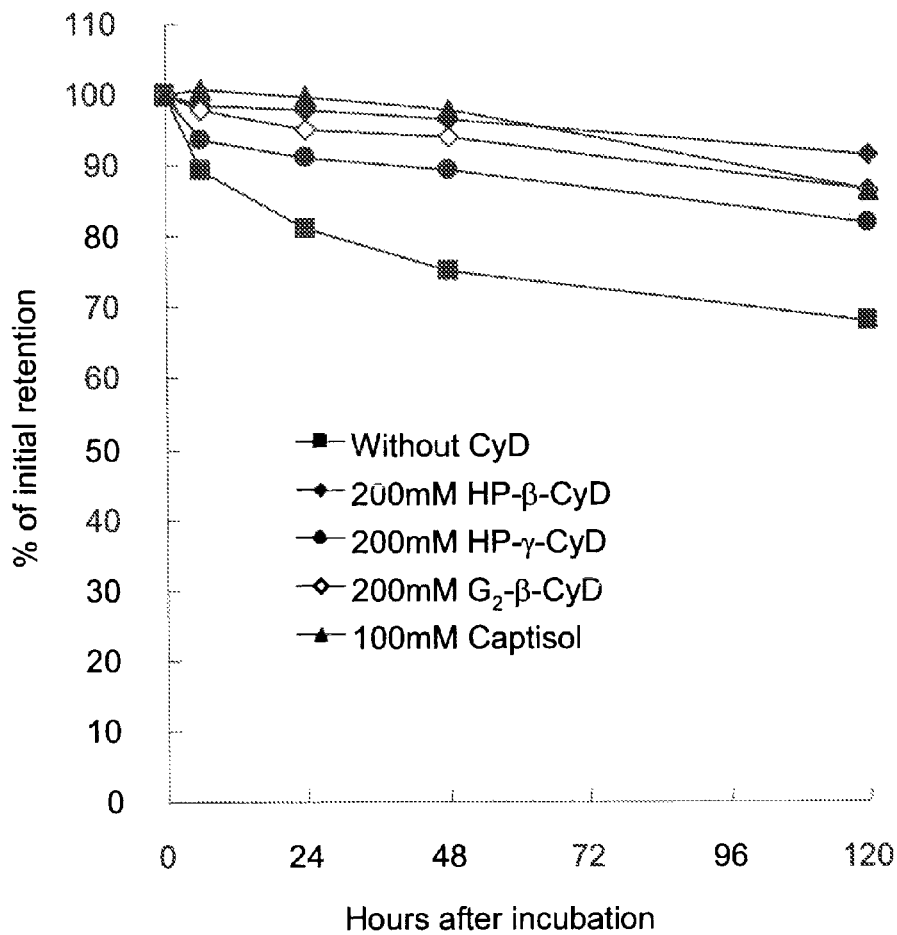
[Fig. 3]
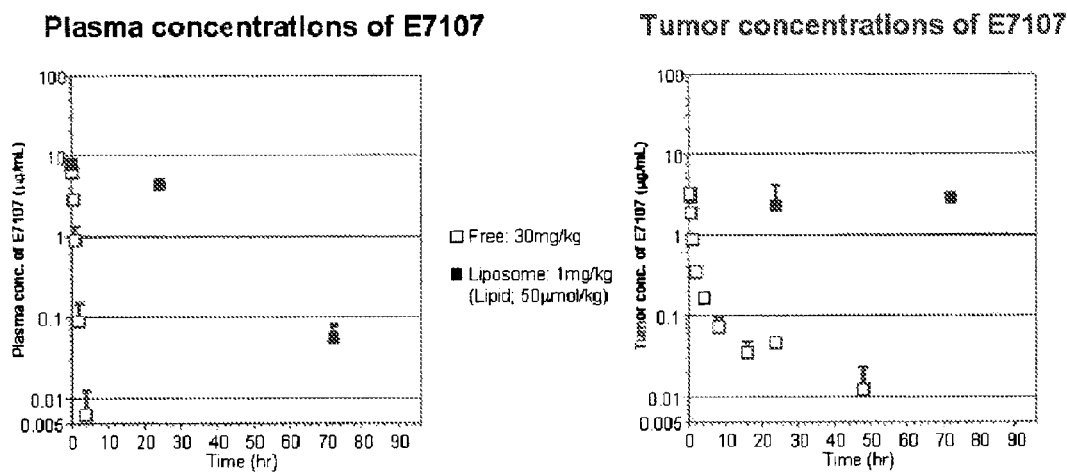

[Fig. 4]
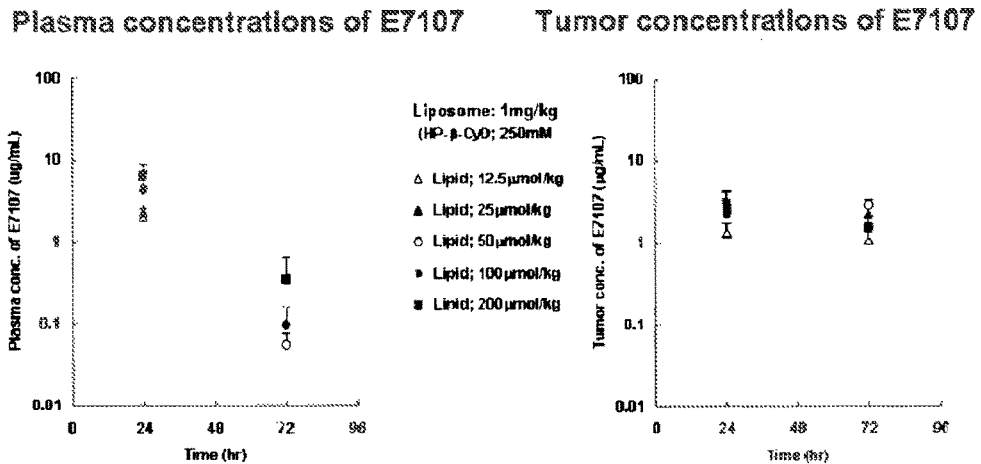
[Fig. 5]
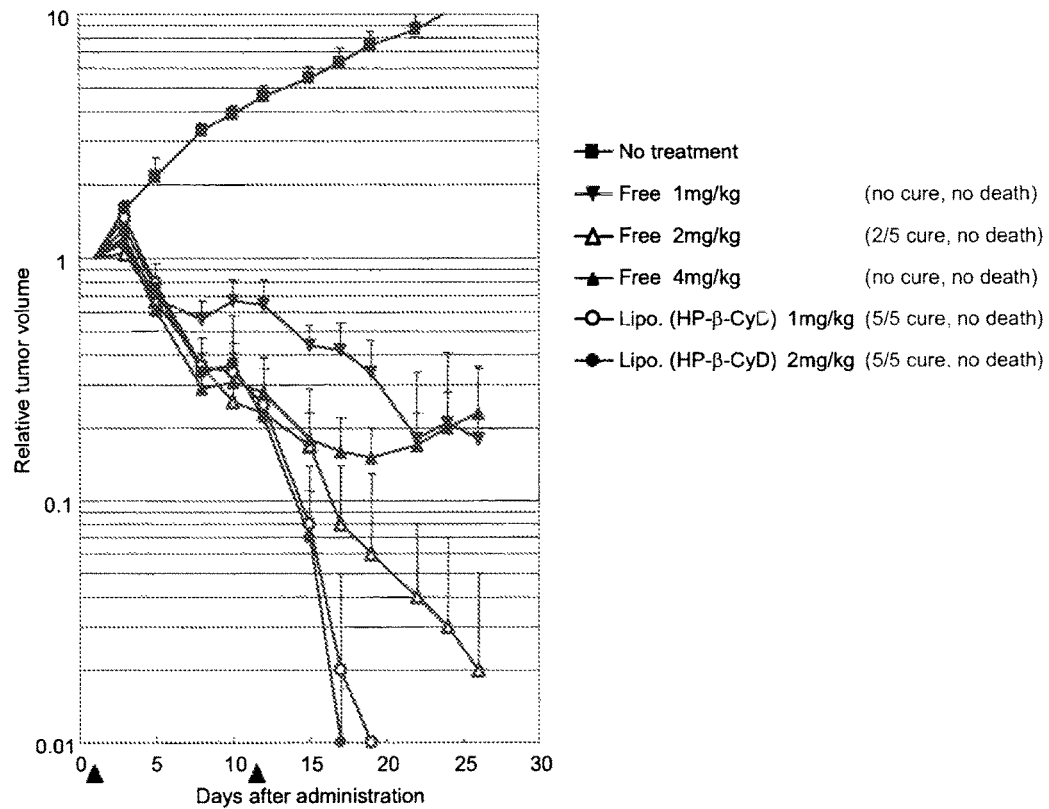

[Fig. 6]
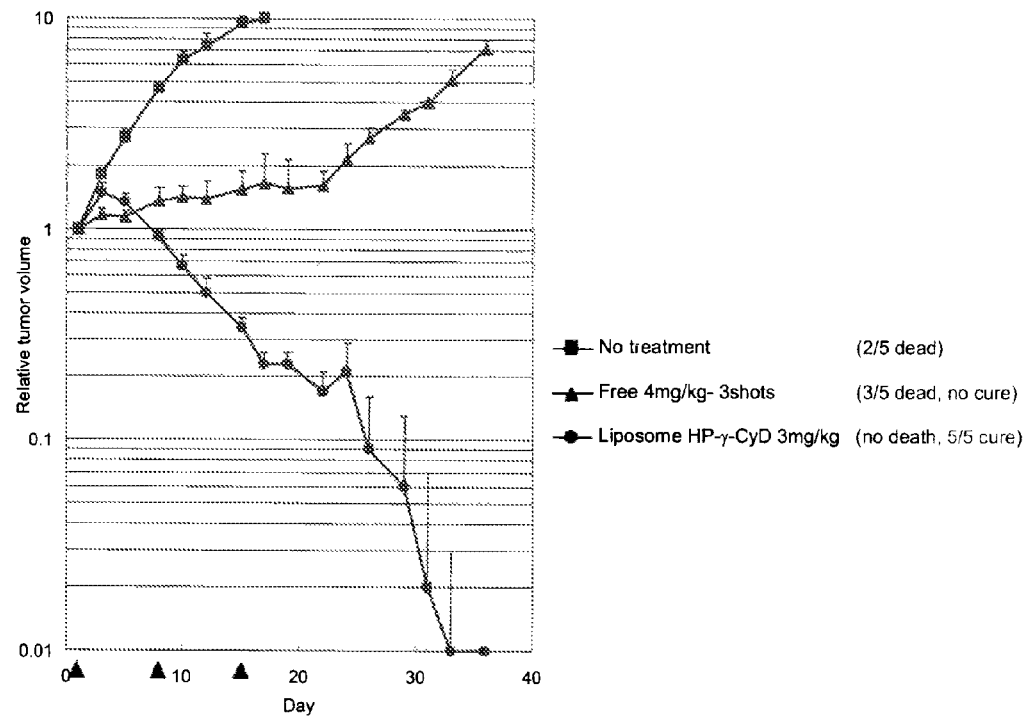
[Fig. 7]
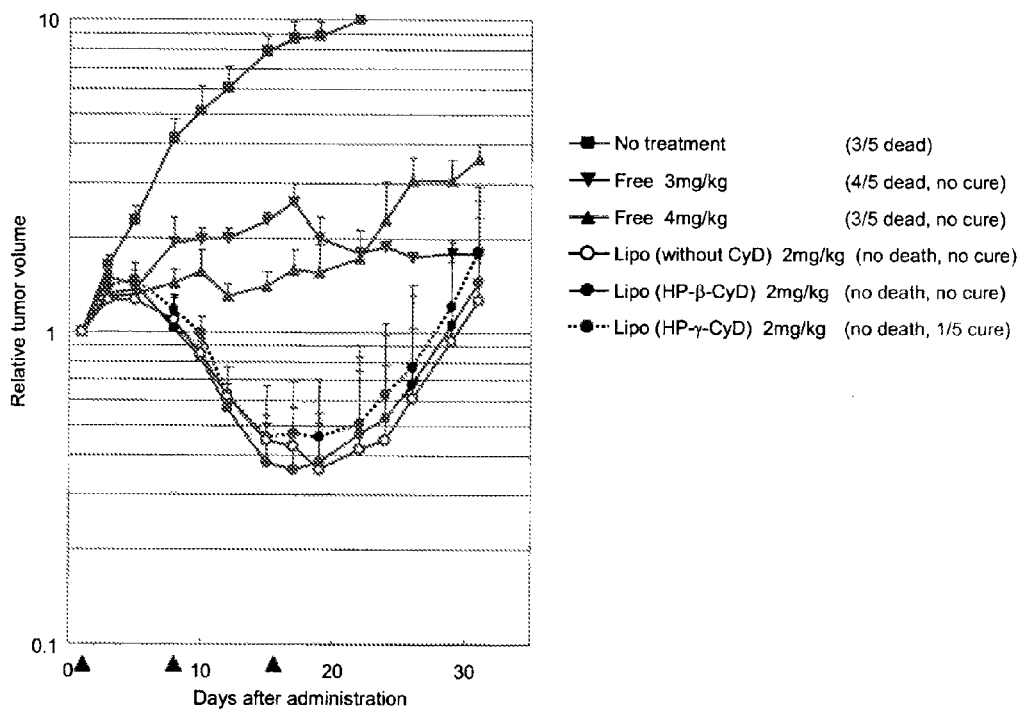

[Fig. 8]
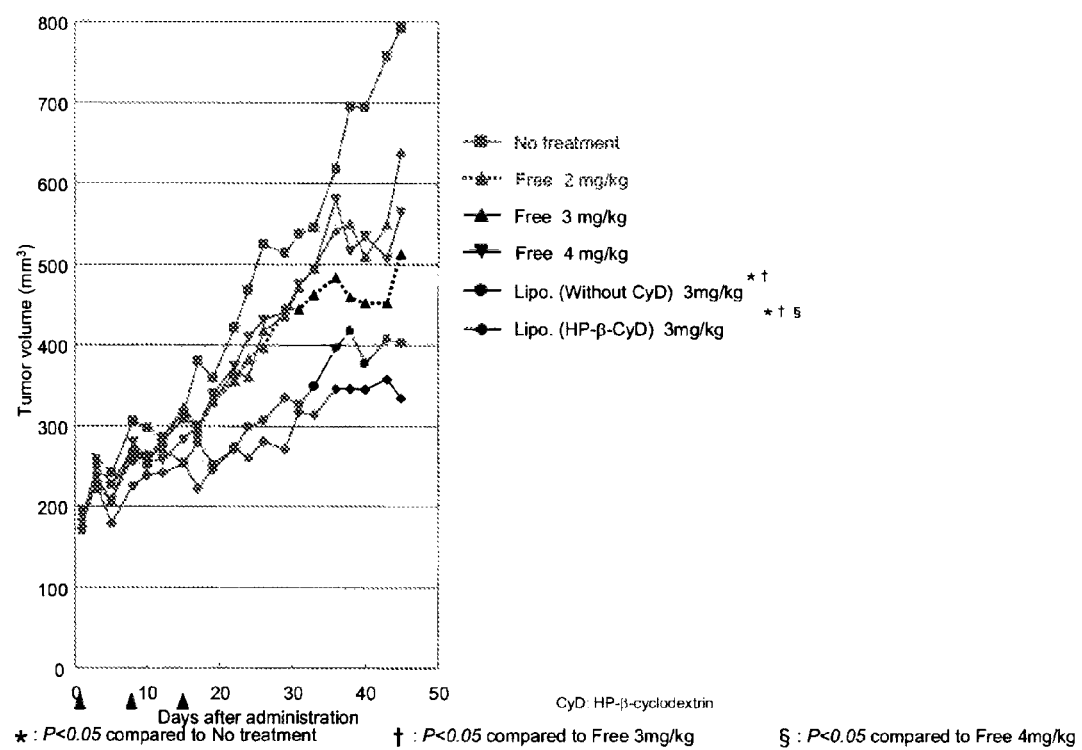

METHOD OF MANUFACTURE OF LIPOSOME COMPOSITION

TECHNICAL FIELD

The present invention relates to a method of manufacture of a liposome composition. The present invention also relates to the liposome composition and a kit for preparing the liposome composition.

BACKGROUND ART

Liposomes are microscopic closed vesicles having an internal phase enclosed by one or more lipid bilayers, and are capable of holding water-soluble material in the internal phase, and lipophilic material in the lipid bilayer. When entrapping an active compound in liposome, and delivering it to target tissue, how to entrap the active compound in the liposome with high efficiency, and how to secure stable retention of the active compound by the liposome constitute important issues.

When entrapping lipophilic compounds in liposome, a high entrapment ratio can be achieved relatively easily, but except in cases of compounds which have very high membrane affinity such as amphotericin B (the principal agent in the liposomal drug AmBisome), retention stability in blood plasma is ordinarily low, and it is difficult to obtain sufficient improvement in pharmacokinetics. With respect to methods for entrapping water-soluble compounds in liposome, there are various methods such as the lipid film method (Vortex method), reverse phase evaporation method, surfactant removal method, freeze-thaw method, and remote loading methods (pH gradient method, ion gradient method). However, it is only the remote loading methods that provide close to a 100% entrapment ratio; an entrapment ratio on the order of only 5 to 30% is obtained from the other methods.

As remote loading methods, those using a pH gradient and ammonium sulfate ion gradient are known. The pH gradient method, which is a remote loading method using a pH gradient, is a technique for incorporating compounds into liposome by using the movement of molecular/ionic dissociation equilibrium due to the pH of the target compound.

As one example of a compound entrapped in liposome by the pH gradient method, one may cite, for example, doxorubicin (DOX, pKa: 8.2). After preparing a liposome solution with a buffer solution of pH 4, the external phase of the liposome is replaced with a pH 7 buffer solution. In the case where DOX is added to this liposome solution, as the molecular DOX in the pH 7 solution is lipophilic, it migrates to the liposome membrane rather than to the aqueous phase. In the case where the DOX that has migrated to the liposome membrane further contacts the pH 4 internal phase of the liposome, it becomes ionic, and is incorporated into the internal phase of the liposome. In this way, DOX is transported from the external phase to the internal phase of liposome by a movement of dissociation equilibrium (see Non-patent Literature 1, Non-patent Literature 2, and Patent Literature 1).

A variety of techniques have been reported for improving this type of remote loading method.

In Non-patent Literature 3, a technique is disclosed for improving the entrapment ratio of active compounds by adding ethanol together with the active compound to the external phase of the liposome, when the pH gradient method is conducted in liposome of special composition called cholesterol-free liposome.

In Patent Literature 2, in addition to the pH gradient, a technique is disclosed for improving the entrapment ratio of active compounds by having copper ions exist in the internal phase of the liposome.

Instead of a pH gradient in the pH gradient method, the ammonium sulfate method, which is a remote loading method using an ammonium sulfate ion gradient, is a technique for incorporating active compounds into the internal phase of liposome by using an ion gradient of bivalent ammonium sulfate (see Non-patent Literature 1 and Patent Literature 3).

In addition to an ion gradient based on ammonium sulfate, Patent Literature 4 discloses a technique for incorporating active compounds into liposome by adding boronic acid together with the active compound to the external phase of the liposome.

Instead of an ion gradient based on ammonium sulfate, Patent Literature 5 discloses a technique wherein, compared to the case where ammonium sulfate is used, the release rate of the active compound is improved by incorporating the active compound into liposome using an ion gradient of glucuronic acid anion.

Thus, from the standpoint of entrapment ratio, remote loading methods are excellent entrapment methods. However, in the case where remote loading methods are used, except for special cases such as Doxil (a liposome preparation of DOX) where the active compound entrapped in the internal phase of the liposome is crystallized, there is the problem that the active compound tends to leak from the liposome in blood plasma, and that retention stability of the active compound is low.

On the other hand, a technique is disclosed for solubilizing in advance an active compound with cyclodextrin (hereinafter, also referred to as "CyD") and then entrapping a complex of the cyclodextrin and the active compound into the liposome by a Vortex method or the like in order to enhance retention stability or enhance the solubility of an active compound. However, this method results in only an entrapment ratio of 5 to 20%, at which large-scale production is very difficult to perform.

In Non-patent Literature 4, a compound is used, in which salicylic acid is covalently bonded to CyD as a model compound, and a lipid film method is adopted for entrapping the compound into the liposome (an entrapment ratio is 8% or lower). It is suggested that the active compound forms a complex with CyD in the liposome internal phase and thus retention stability is enhanced.

In Non-patent Literature 5, a poorly water-soluble compound betamethasone is solubilized in advance with several types of CyD derivatives and entrapped into the liposome by a lipid film method (an entrapment ratio is 3% or lower). It is indicated that retention stability is enhanced and thus slow release effect is provided by the use of CyD derivatives having a high association constant with betamethasone.

Moreover, in Non-patent Literature 6, a poorly water-soluble compound ketoprofen is solubilized in advance with HP-β-cyclodextrin, and various entrapment methods have been attempted for the obtained complex. MLVs (multilamellar vesicles) achieve a relatively high entrapment ratio of approximately 75%, whereas SUVs (small unilamellar vesicles), which are used with the aim of EPR effect, remain at an entrapment ratio of approximately 55%. However, entrapment into the liposome internal phase with such a high entrapment ratio is theoretically impossible by the entrapment methods used in the document. Thus, the ketoprofen is highly likely to be distributed in the lipid bilayer, not in the liposome internal water phase.

Furthermore, Non-patent Literature 7 discloses that the liposome membrane permeability of a water-soluble substance is enhanced by creating in advance a complex of prednisolone and CyD and entrapping the complex into a liposome by a freeze-thaw method.

Non-patent Literature 8 discloses that the liposome entrapping the complex of DOX and γ-cyclodextrin exhibits a higher intratumoral DOX concentration and antitumor effect than those of the liposome entrapping only DOX. In said document as well, the complex of DOX and γ-cyclodextrin is formed in advance, and this complex is entrapped in the liposome. Likewise, in Patent Literature 6, a technique is disclosed for achieving slow release of an active compound by forming in advance the complex of the water-soluble compound and CyD and thus entrapping this complex into the liposome.

As described above, with conventional technical methods, the current situation is that it is difficult to achieve coexistence of a high entrapment ratio of the active compound in liposome and retention stability of the active compound in liposome.

PRIOR ART LITERATURE

Patent Literature

Patent Literature 1: U.S. Pat. No. 5,192,549, Specification
Patent Literature 2: PCT International Publication WO 2006/037230, Pamphlet
Patent Literature 3: U.S. Pat. No. 5,316,771, Specification
Patent Literature 4: U.S. Pat. No. 6,051,251, Specification
Patent Literature 5: PCT International Publication WO 2005/046643, Pamphlet
Patent Literature 6: PCT International Publication WO 94/23697, Pamphlet Non-Patent Literature Non-patent Literature 1: Yasuyuki Sazuka, "Liposome Preparation Method," "New Developments in Liposome Application: Toward the Development of Artificial Cells" (Kazunari Akiyoshi, Shigeru Tsujii, editorial supervision)" NTS, (2005), pp. 33-37.
Non-patent Literature 2: Mayer L D et al., Biochimica et Biophysica Acta, (1986), 857: pp. 123-126.
Non-patent Literature 3: N. Dos Santos et al., Biochimica et Biophysica Acta, (2004), 1661(1): pp. 47-60.
Non-patent Literature 4: Y. Hagiwara et al., Chem. Pharm. Bull., (2006), 54(1):pp. 26-32
Non-patent Literature 5: G. Piel et al., International Journal of Pharmaceutics, (2006), 312: pp. 75-82
Non-patent Literature 6: F. Maestrelli et al., International Journal of Pharmaceutics, (2006), 312:pp. 53-60
Non-patent Literature 7: D. G. Fatouros et al., European Journal of Pharmaceutical Sciences, (2001), 13:pp. 287-296
Non-patent Literature 8: H. Arima et al., Journal of Drug Targeting, 2006, 14(4):pp. 225-232

OUTLINE OF THE INVENTION

Problem to be Solved by the Invention

The object of the present invention is to provide a method of manufacture of a liposome having high retention stability of an active compound with a high entrapment ratio.

Means for Solving the Problem

As a result of diligent research aimed at solving the aforementioned problems, the present inventors discovered, surprisingly, that an active compound added to a liposome external phase moves to a liposome internal phase by entrapping in advance cyclodextrin in the liposome internal phase and can thus be entrapped in the liposome internal phase with an extremely high entrapment ratio, and with respect to the obtained liposome composition, the retention stability of the active compound is extremely high.

Namely, the present invention is as follows:

[1] A method of manufacture of a liposome composition, including:
a step in which a liposome dispersion liquid containing a liposome, and further containing cyclodextrin in the liposome internal phase is provided;
a step in which said liposome dispersion liquid is mixed with an active compound; and
a step in which said active compound is introduced into the liposome internal phase of said liposome dispersion liquid.

[2] The method according to 1, wherein said liposome dispersion liquid contains a higher concentration of cyclodextrin in the liposome internal phase than in the liposome external phase.

[3] The method according to 1 or 2, wherein said liposome dispersion liquid does not substantially contain cyclodextrin in the liposome external phase.

[4] The method according to any one of 1 to 3, wherein the step in which said liposome dispersion liquid is provided includes:
a step in which a liposome preparatory liquid containing liposome, and further containing said cyclodextrin in the liposome internal phase and the liposome external phase; and
a step in which the liposome external phase of said liposome preparatory liquid is substituted or diluted so as to adjust the concentration of said cyclodextrin in the liposome external phase.

[5] The method according to any one of 1 to 4, wherein said introducing step includes:
a step in which liposome membrane permeability in a mixed solution obtained in the mixing step is enhanced.

[6] The method according to any one of 1 to 5, wherein said introducing step includes:
a step in which the mixed solution is heated to a temperature equal to or higher than a phase transition temperature of the liposome lipid bilayer.

[7] A liposome composition manufactured by a method according to any one of 1 to 6.

[8] The liposome composition according to 7, wherein said active compound is an antitumor agent.

[9] A liposome composition containing liposome, and further containing cyclodextrin and an active compound in the liposome internal phase, wherein the active compound is selected from the group consisting of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide (E7107), eribulin, doxorubicin, epirubicin, pirarubicin, daunorubicin, docetaxel, and paclitaxel, and pharmacologically permissible salts of the foregoing.

[10] The liposome composition according to 9, wherein said active compound is eribulin mesylate.

[11] The liposome composition according to any one of 7 to 10, wherein said liposome composition is in a solid or liquid form.

[12] A kit for preparing a liposome composition containing an active compound in the liposome internal phase, containing:
a liposome reagent containing liposome, and further containing cyclodextrin in the liposome internal phase.

[13] The kit according to 12, wherein said liposome reagent is in a solid or liquid form.

[14] The kit according to 12 or 13, containing said liposome reagent, and further containing an active compound.

[15] The kit according to 14, wherein said active compound is an antitumor agent.

Effect of the Invention

According to the present invention, it is possible to offer a method of manufacture of a novel liposome composition. The method of manufacture of liposome of the present invention allows an active compound to be entrapped in the liposome internal phase with a high degree of efficiency. In addition, liposome manufactured by the method has a high retention stability of the active compound.

BRIEF DESCRIPTION OF DRAWINGS

FIG. 1 shows the in vitro retention stability of E7107 in rat blood plasma (37° C.).

FIG. 2 shows the in vitro retention stability of eribulin mesylate in rat blood plasma (37° C.).

FIG. 3 shows the in vivo blood retention and tumor migration of E7107 in WiDr cancer-bearing nude mice.

FIG. 4 shows the in vivo blood retention and tumor migration of E7107 in WiDr cancer-bearing nude mice.

FIG. 5 shows the in vivo antitumor activity of eribulin mesylate due to liposome in WiDr cancer-bearing nude mice.

FIG. 6 shows the in vivo antitumor activity of eribulin mesylate due to liposome in FaDu cancer-bearing nude mice.

FIG. 7 shows the in vivo antitumor activity of eribulin mesylate due to liposome in FaDu cancer-bearing nude mice.

FIG. 8 shows the in vivo antitumor activity of eribulin mesylate due to liposome in ACHN cancer-bearing nude mice.

BEST MODE FOR CARRYING OUT OF THE INVENTION

The present invention is specifically described by modes for carrying out the invention, but the present invention is not limited to the following modes for carrying out the invention, and may be carried out with a variety of modifications.

The contents disclosed in the literature referenced in the present invention are incorporated into the present invention as reference.

[Definitions]

"Liposome" means microscopic closed vesicles having an internal phase enclosed by lipid bilayer. In the present invention, liposome includes small single-membrane liposome (SUV: small unilamellar vesicle), large single-membrane liposome (LUV: large unilamellar vesicle), still larger single-membrane liposome (GUV: giant unilamellar vesicle), multilayer liposome having multiple concentric membranes (MLV: multilamellar vesicle), liposome having multiple membranes that are not concentric, but irregular (MVV: multivesicular vesicle), etc.

"Liposome internal phase" means an aqueous region enclosed in the lipid bilayer of the liposome, and is used with the same meaning as "internal water phase" and "liposome internal water phase." "Liposome external phase" means the region not enclosed by the lipid bilayer of the liposome (that is, the region apart from the internal phase and the lipid bilayer) in the case where the liposome is dispersed in liquid.

"Liposome composition" means a composition that contains liposome and that further contains cyclodextrin and an active compound in the liposome internal phase. In the present invention, liposome composition includes both solid and liquid forms.

"Liposome dispersion liquid" means a composition containing liposome, and further containing cyclodextrin in the liposome internal phase and is a composition preceding the introduction of the active compound into the liposome internal phase, though the cyclodextrin concentration of the liposome external phase has already been adjusted. The adjustment of the cyclodextrin concentration in the liposome external phase is described later, and as the liposome dispersion liquid, one may cite a dispersion liquid in which the cyclodextrin concentration in the liposome external phase is lower than the concentration in the liposome internal phase and a dispersion liquid that does not substantially contain cyclodextrin in the liposome external phase.

In this context, when cyclodextrin-induced improvement in the solubility (nominal solubility) of the active compound is significantly confirmed, this is referred to as "substantially containing cyclodextrin", whereas the "liposome external phase does not substantially contain cyclodextrin" means that the liposome external phase does not contain cyclodextrin in an amount in which cyclodextrin-induced improvement in the solubility (nominal solubility) of the active compound is significantly confirmed.

"Liposome preparatory solution" means a composition containing liposome, and further containing cyclodextrin in the liposome internal phase and the liposome external phase, and is a composition preceding adjustment of the cyclodextrin concentration of the liposome external phase.

"Liposome reagent" means a liposome dispersion liquid, in the case where it is in a liquid form. In the case where it is in a solid form, it means a reagent from which liposome dispersion liquid can be obtained by dissolution or suspension in a prescribed solvent. The solvent is described below. As described below, a solid liposome reagent can be obtained, for example, by drying a liposome dispersion liquid.

In the present specification, "the mixing of solid and liquid" includes the dissolution and suspension of the solid in the liquid, and mixing, dissolution and suspension are used in a mutually interchangeable manner. Similarly, solvent and dispersion medium are also used in a mutually interchangeable manner.

[Active Compounds]

There are no particular limitations on the active compound in the present invention, so long as the active compound forms a complex with cyclodextrin. As active compounds, one may choose from among compounds used in the fields of medicines (including diagnostic drugs), cosmetic products, food products, and so on. With respect to active compounds, it is acceptable to combine one or more compounds.

As active compounds, one may cite low-molecular compounds, etc. Among these, compounds used as antitumor agents, antibacterial agents, anti-inflammatory agents, anti-myocardial infarction agents, and contrast agents are suitable.

With respect to the molecular weight of the active compound, a range of 100 to 2000 is preferable, a range of 200 to 1500 is more preferable, and a range of 300 to 1000 is even more preferable. Within these ranges, the liposome membrane permeability of the active compound is generally satisfactory, and the present invention may be suitably applied.

The active compound includes water-soluble and lipophilic compounds, so long as they are more or less soluble in water or aqueous solvents, the present invention may be applied.

Moreover, the present invention utilizes the interaction between the active compound and the cyclodextrin, as described later, and the present invention can be applied to any active compound that has higher solubility (nominal solubility) in the presence of cyclodextrin than in the absence of cyclodextrin. Without being bound by theory, it is thought that the whole or a portion of the active compound molecule is included in the internal space (pore) of the cyclodextrin ring structure and thus the solubility (nominal solubility) of the active compound results in higher than the solubility in water or aqueous solvents free from cyclodextrin. For example, it is said that α-cyclodextrin has pores of 0.45 to 0.6 nm in inside diameter; β-cyclodextrin allegedly has pores of 0.6 to 0.8 nm in inside diameter; and γ-cyclodextrin allegedly has pores of 0.8 to 0.95 nm in inside diameter. When the active compound has a region (particularly, a hydrophobic region) capable of interacting with (or being included in) the pores having these inside diameters, it is thought that the solubility of this active compound is enhanced in the presence of cyclodextrin.

Moreover, cyclodextrins such as hydroxy-β-cyclodextrin, hydroxypropyl-β-cyclodextrin, and sulfobutyl ether-β-cyclodextrin have been obtainable in recent years, and even these cyclodextrins can enhance the solubility of the active compound. However, in the case of these cyclodextrins, it is known that the enhancement in the solubility of the active compound is not always attributed to inclusion in the internal space (pore) of the cyclodextrin ring structure but is attributed to the intermolecular interaction with hydroxy groups or sulfobutyl ether groups. In the present invention, such enhancement in solubility based on the intermolecular interaction is also acceptable.

There are no particular limitations on antitumor agents in the present invention, and one may cite, for example, camptothecin derivatives such as irinotecan hydrochloride, nogitecan hydrochloride, exatecan, RFS-2000, lurtotecan, BNP-1350, Bay-383441, PNU-166148, IDEC-132, BN-80915, DB-38, DB-81, DB-90, DB-91, CKD-620, T-0128, ST-1480, ST-1481, DRF-1042, DE-310; taxane derivatives such as docetaxel hydride, docetaxel, pacritaxel, IND-5109, BMS-184476, BMS-188797, T-3782, TAX-1011, SB-RA-31012, SBT-1514, and DJ-927; iphosphamide, nimstine hydrochloride, carvocon, cyclophosphamide, dacarbazine, thiotepa, busulfan, melfaran, ranimustine, estramustine phosphate sodium, 6-mercaptopurine riboside, enocitabine, gemcitabine hydrochloride, carmfur, cytarabine, cytarabine ocfosfate, tegafur, doxifluridine, hydroxycarbamide, fluorouracil, methotrexate, mercaptopurine, fludarabine phosphate, actinomycin D, aclarubicin hydrochloride, idarubicin hydrochloride, pirarubicin hydrochloride, epirubicin hydrochloride, daunorubicin hydrochloride, doxorubicin hydrochloride, epirubicin, pirarubicin, daunorubicin, doxorubicin, pirarubicin hydrochloride, bleomycin hydrochloride, zinostatin stimalamer, neocarzinostatin, mitomycin C, bleomycin sulfate, peplomycin sulfate, etoposide, vinorelbine tartrate, vincrestine sulfate, vindesine sulfate, vinblastine sulfate, amrubicin hydrochloride, gefinitib, exemestane, capecitabine, TNP-470, TAK-165, KW-2401, KW-2170, KW-2871, KT-5555, KT-8391, TZT-1027, S-3304, CS-682, YM-511, YM-598, TAT-59, TAS-101, TAS-102, TA-106, FK-228, FK-317, E7070, (8E, 12E,14E)-7-[(4-cycloheptylpiperazine-1-yl)carbonyl]oxy-3, 6,16,21-tetrahydroxy-6,10,12,16,20-pentamethyl-18,19-epoxytricosa-8,12,14-trien-1'-olide (E7107), eribulin, eribulin mesylate, KRN-700, KRN-5500, J-107088, HMN-214, SM-11355, ZD-0473, etc. With respect to the compounds recorded as salts among the aforementioned antitumor agents, any salt is acceptable, and free bodies are also acceptable. With respect to compounds recorded as free bodies, any salt is acceptable. The active compound is selected from the group consisting of the compounds described above or their pharmacologically permissible salts and, for example, selected from the group consisting of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide (E7107), eribulin, doxorubicin, epirubicin, pirarubicin, daunorubicin, docetaxel, and paclitaxel, and pharmacologically permissible salts of the foregoing.

There are no particular limitations on antibacterial agents, and one may cite, for example, amfotericine B, cefotiam hexyl, cephalosporin, chloramphenicol, diclofenac, etc. With respect to compounds of the aforementioned antibacterial agents, any salt is acceptable.

There are no particular limitations on anti-inflammatory agents, and one may cite, for example, prostaglandins (PGE1, PGE2), dexamethasone, hydrocortisone, pyroxicam, indomethacin, prednisolone, etc. With respect to compounds of the aforementioned anti-inflammatory agents, any salt is acceptable.

There are no particular limitations on anti-myocardial infarction agents, and one may cite, for example, adenosine, atenolol, pilsicamide, etc. With respect to compounds of the aforementioned anti-myocardial infarction agents, any salt is acceptable.

There are not particular limitations on the contrast agents, and one may cite, for example, iopamidol, ioxaglic acid, iohexyl, iomeprol, etc. With respect to the contrast agents, any salt is acceptable.

[Cyclodextrin]

In the present invention, there are no particular limitations on the cyclodextrin, so long as cyclodextrin forms a complex with the active compound. Cyclodextrin is cyclic compound α-(1,4) bonded with plural glucose units and may have various substituents. Cyclodextrins constituted by 6, 7, and 8 glucose units (called α-, β-, and γ-cyclodextrins, respectively) and derivatives thereof are stable and thus preferable.

The cyclodextrin can be selected appropriately according to the active compound, etc. Specifically, it is preferable that the cyclodextrin itself have high solubility in water. This facilitates entrapment of a larger amount of the cyclodextrin in the liposome internal phase. More specifically, with respect to the water solubility of the cyclodextrin, 10 mg/mL or higher is preferable, 50 mg/mL or higher is more preferable, and 100 mg/mL or higher is even more preferable.

Moreover, with respect to the cyclodextrin, a large association constant with the active compound is preferable. For example, a higher association constant can be obtained by selecting the number of glucose units in cyclodextrin according to the size of the active compound. Moreover, when the association constant depends on pH, it is preferable that the cyclodextrin is selected such that the association constant becomes large at the pH of the liposome internal phase. As a result, the solubility (nominal solubility) of the active compound in the presence of cyclodextrin can be further improved. Specifically, with respect to the association constant of the cyclodextrin with the active compound, 100 or higher is preferable, and 1000 or higher is more preferable.

Furthermore, one can select preferable cyclodextrin according to the safety or filed-proven results of cyclodextrin itself, etc., depending on the purpose.

Specifically, as the cyclodextrin, one may cite, for example, α-cyclodextrin, β-cyclodextrin, γ-cyclodextrin, hexakis(2,3,6-tri-O-acetyl)-α-cyclodextrin, heptakis(2,3,6-tri-O-acetyl)-β-cyclodextrin, octakis(2,3,6-tri-O-acetyl)-γ-cyclodextrin, acetylated α-cyclodextrin, acetylated β-cyclodextrin, acetylated γ-cyclodextrin, hexakis(2,3,6-tri-O-methyl)-α-cyclodextrin, heptakis(2,3,6-tri-O-methyl)-β-cyclodextrin, octakis(2,3,6-tri-O-methyl)-γ-cyclodextrin, hexakis(2,6-di-O-methyl)-α-cyclodextrin, heptakis(2,6-di-O-methyl)-β-cyclodextrin, octakis(2,6-di-O-methyl)-γ-cyclodextrin, partially methylated α-cyclodextrin, partially methylated β-cyclodextrin, partially methylated γ-cyclodextrin, hydroxy)propyl-α-cyclodextrin, 2-O-(2-hydroxy)propyl-β-cyclodextrin, hydroxy)propyl-γ-cyclodextrin, (2-hydroxy)propyl-α-cyclodextrin (hydroxypropyl-α-cyclodextrin, HP-α-cyclodextrin), (2-hydroxy)propyl-β-cyclodextrin (hydroxypropyl-β-cyclodextrin, HP-β-cyclodextrin), (2-hydroxy)propyl-γ-cyclodextrin (hydroxypropyl-γ-cyclodextrin, HP-γ-cyclodextrin), carboxylmethylated α-cyclodextrin, carboxylmethylated β-cyclodextrin, carboxylmethylated γ-cyclodextrin, succinylated α-cyclodextrin, succinylated β-cyclodextrin, succinylated γ-cyclodextrin, heptakis(3-O-allyl-2,6-di-O-methyl)-β-cyclodextrin, carboxyethylated α-cyclodextrin, carboxyethylated β-cyclodextrin, carboxyethylated γ-cyclodextrin, hexakis(2,6-di-O-n-pentyl)-α-cyclodextrin, heptakis(2,6-di-O-n-pentyl)-β-cyclodextrin, octakis(2,6-di-O-n-pentyl)-γ-cyclodextrin, hexakis(3-O-n-butyl-2,6-di-O-n-pentyl)-α-cyclodextrin, heptakis(3-O-n-butyl-2,6-di-O-n-pentyl)-β-cyclodextrin, octakis(3-O-n-butyl-2,6-di-O-n-pentyl)-γ-cyclodextrin, heptakis(2,6-di-O-n-butyl)-β-cyclodextrin, n-butylated α-cyclodextrin, n-butylated β-cyclodextrin, n-butylated γ-cyclodextrin, hexakis(2,3,6-tri-O-benzoyl)-α-cyclodextrin, heptakis(2,3,6-tri-O-benzoyl)-β-cyclodextrin, octakis(2,3,6-tri-O-benzoyl)-γ-cyclodextrin, palmitylated β-cyclodextrin, 6-O-monotosylated β-cyclodextrin, ethylated α-cyclodextrin, ethylated β-cyclodextrin, ethylated γ-cyclodextrin, heptakis(2,6-di-O-ethyl)-β-cyclodextrin, hexakis(2,3,6-tri-O-ethyl)-α-cyclodextrin, heptakis(2,3,6-tri-O-ethyl)-β-cyclodextrin, octakis (2,3,6-tri-O-ethyl)-γ-cyclodextrin, 6-monodeoxy-6-monoamino-β-cyclodextrin hydrochloride, hexakis(3-O-acetyl-2,6-di-O-n-pentyl)-α-cyclodextrin, heptakis(3-O-acetyl-2,6-di-O-n-pentyl)-β-cyclodextrin, octakis(3-O-acetyl-2,6-di-O-n-pentyl)-γ-cyclodextrin, hexakis(2,6-di-O-n-pentyl-3-O-trifluoroacetyl)-α-cyclodextrin, heptakis(2,6-di-O-n-pentyl-3-O-trifluoroacetyl)-β-cyclodextrin, octakis(2,6-di-O-n-pentyl-3-O-trifluoroacetyl)-γ-cyclodextrin, hexakis(2,6-di-O-methyl-3-O-n-pentyl)-α-cyclodextrin, heptakis (2,6-di-O-methyl-3-O-n-pentyl)-β-cyclodextrin, octakis(2,6-di-O-methyl-3-O-n-pentyl)-γ-cyclodextrin, (2-hydroxy)ethylated α-cyclodextrin, (2-hydroxy)ethylated β-cyclodextrin, (2-hydroxy)ethylated γ-cyclodextrin, hexakis(2,3,6-tri-O-n-octyl)-α-cyclodextrin, heptakis(2,3,6-tri-O-n-octyl)-β-cyclodextrin, octakis(2,3,6-tri-O-n-octyl)-γ-cyclodextrin, hexakis (2,3-di-O-acetyl-6-O-tert-butyldimethylsilyl)-α-cyclodextrin, heptakis(2,3-di-O-acetyl-6-O-tert-butyldimethylsilyl)-β-cyclodextrin, octakis(2,3-di-O-acetyl-6-O-tert-butyldimethylsilyl)-γ-cyclodextrin, succinylated (2-hydroxy)propyl-α-cyclodextrin, succinylated (2-hydroxy)propyl-β-cyclodextrin, succinylated (2-hydroxy)propyl-γ-cyclodextrin, hexakis(6-O-tert-butyldimethylsilyl)-α-cyclodextrin, heptakis(6-O-tert-butyldimethylsilyl)-β-cyclodextrin, octakis(6-O-tert-butyldimethylsilyl)-γ-cyclodextrin, hexakis(6-O-tert-butyldimethylsilyl-2,3-di-O-methyl)-α-cyclodextrin, heptakis(6-O-tert-butyldimethylsilyl-2,3-di-O-methyl)-β-cyclodextrin, octakis(6-O-tert-butyldimethylsilyl-2,3-di-O-methyl)-γ-cyclodextrin, hexakis(2,6-di-O-tert-butyldimethylsilyl)-α-cyclodextrin, heptakis(2,6-di-O-tert-butyldimethylsilyl)-β-cyclodextrin, octakis(2,6-di-O-tert-butyldimethylsilyl)-γ-cyclodextrin, octamesitylene-γ-cyclodextrin, hexakis(2,3,6-tri-O-trifluoroacetyl)-α-cyclodextrin, heptakis(2,3,6-tri-O-trifluoroacetyl)-β-cyclodextrin, octakis(2,3,6-tri-O-trifluoroacetyl)-γ-cyclodextrin, sulfopropylated α-cyclodextrin, sulfopropylated β-cyclodextrin, sulfopropylated γ-cyclodextrin, 6-O-monomaltosyl-β-cyclodextrin, 6-O-maltosyl-β-cyclodextrin (so-called G2-β-cyclodextrin), (2-carbomethoxy)propoxy-β-cyclodextrin, heptakis(3-O-acetyl-2,6-di-O-n-butyl)-β-cyclodextrin, (2-cyano)ethyl-α-cyclodextrin, (2-cyano)ethyl-β-cyclodextrin, (2-cyano)ethyl-γ-cyclodextrin, 6-monodeoxy-6-monoazido-β-cyclodextrin, 6-monodeoxy-6-monoiodo-β-cyclodextrin, 6A,6E-dideoxy-6A,6B-diiodo-β-cyclodextrin, 6-monodeoxy-6-monobromo-β-cyclodextrin, 6A,6B-dideoxy-6A,6B-dibromo-β-cyclodextrin, sulfobutylether-β-cyclodextrin (so-called SBE-β-cyclodextrin; CAPTISOL), etc. It is also acceptable to combine one or more of these cyclodextrins.

Among them, highly water-soluble cyclodextrins are preferable. More preferably, one may cite α-cyclodextrin, γ-cyclodextrin, HP-α-cyclodextrin, HP-β-cyclodextrin, HP-γ-cyclodextrin, G2-β-cyclodextrin, and SBE-β-cyclodextrin, even more preferably α-cyclodextrin, HP-β-cyclodextrin, and SBE-β-cyclodextrin.

[Lipids]

It is preferable that the membrane constituents of the liposome of the present invention include phospholipids and/or phospholipid derivatives. As phospholipids and phospholipid derivatives, one may cite, for example, phosphatidyl ethanolamine, phosphatidyl choline, phosphatidyl serine, phosphatidyl inositol, phosphatidyl glycerol, cardiolipin, sphingomyelin, ceramide phosphorylethanolamine, ceramide phosphoryl glycerol, ceramide phosphoryl glycerol phosphate, 1,2-dimyristoyl-1,2-deoxyphosphatidyl choline, plasmalogen, phosphatidic acid, etc. It is also acceptable to combine one or more of these phospholipids and phospholipid derivatives.

There are no particular limitations on fatty-acid residues in the phospholipids and phospholipid derivatives, and one may cite, for example, saturated or unsaturated fatty-acid residue with a carbon number of 12 to 20. Specifically, one may cite acyl groups derived from fatty-acid such as lauric acid, myristic acid, palmitic acid, stearic acid, oleic acid, and linoleic acid. One may also use phospholipids derived from natural substances such as egg-yolk lecithin and soy lecithin, partially hydrogenated egg-yolk lecithin, (completely) hydrogenated egg-yolk lecithin, partially hydrogenated soy lecithin, and (completely) hydrogenated soy lecithin whose unsaturated fatty-acid residues are partially or completely hydrogenated, etc.

There are no particular limitations on the mixing amount (mole fraction) of the phospholipids and/or phospholipid derivatives that are used when preparing the liposome, but 10 to 80% relative to the entire liposome membrane composition is preferable, and 30 to 60% is more preferable.

With respect to membrane constituents, apart from phospholipids and/or phospholipid derivatives, the liposome of the present invention may also include sterols such as cholesterol and cholestanol as membrane stabilizers, fatty acids having saturated or unsaturated acyl groups with a carbon number of 8 to 22, and antioxidants such as α-tocopherol.

There are no particular limitations on the mixing amount (mole fraction) of these sterols that are used when preparing the liposome, but 1 to 60% relative to the entire liposome membrane composition is preferable, 10 to 50% is more preferable, and 30 to 50% is even more preferable. Moreover, there are no particular limitations on the mixing amount (mole fraction) of the fatty acids, but 0 to 30% relative to the entire liposome membrane composition is preferable, 0 to 20% is more preferable, and 0 to 10% is even more preferable. With respect to the mixing amount (mole fraction) of the antioxidants, it is sufficient if an amount is added that can obtain the antioxidant effect, but 0 to 15% of the entire liposome membrane composition is preferable, 0 to 10% is more preferable, and 0 to 5% is even more preferable.

The liposome of the present invention may also contain functional lipids and modified lipids as membrane constituents.

As functional lipids, one may cite lipid derivatives retained in blood, temperature-sensitive lipid derivatives, pH-sensitive lipid derivatives, etc. As modified lipids, one may cite PEG lipids, sugar lipids, antibody-modified lipids, peptide-modified lipids, etc.

As lipid derivatives retained in blood, one may cite, for example, glycophorin, ganglioside GM1, ganglioside GM3, glucuronic acid derivatives, glutaminic acid derivatives, polyglycerin phospholipid derivatives, polyethylene glycol derivatives (methoxypolyethylene glycol condensates, etc.) such as N-[carbonyl-methoxy polyethylene glycol-2000]-1,2-dipalmitoyl-sn-glycero-3-phosphoethanolamine, N-[carbonyl-methoxy polyethylene glycol-5000]-1,2-dipalmitoyl-sn-glycero-3-phosphoethanolamine, N-[carbonyl-methoxy polyethylene glycol-750]-1,2-distearoyl-sn glycero-3-phosphoethanolamine, N-[carbonyl-methoxy polyethylene glycol-2000]-1,2-distearoyl-sn-glycero-3-phosphoethanolamine (MPEG 2000-distearoyl phosphatidyl ethanolamine), and N-[carbonyl-methoxy polyethylene glycol-5000]-1,2-distearoyl-sn-glycero-3-phosphoethanolamine, which are condensates of phosphoethanolamine and methoxy polyethylene glycol. By having the liposome contain lipid derivatives retained in blood, it is possible to improve the blood retention of the liposome, because the liposome becomes difficult to capture in the liver, etc. as a foreign impurity.

As temperature-sensitive lipid derivatives, one may cite, for example, dipalmitoyl phosphatidylcholine, etc. By having the liposome contain temperature-sensitive lipid derivatives, it is possible to cause destruction of liposome at specific temperatures, and cause changes in the surface properties of the liposome. Furthermore, by combining this with an increase in temperature at the target site of the tumor, etc., it is possible to destroy the liposome at the target site, and release the active compound at the target site.

As pH-sensitive lipid derivatives, one may cite, for example, dioleoyl phosphatidyl ethanolamine, etc. By having the liposome contain pH-sensitive lipid derivatives, it is possible to promote membrane fusion of liposome and endosome when the liposome is incorporated into cells due to the endocytosis, and improve transmission of the active compound to the cytoplasm.

As sugar lipids, antibody-modified lipids, and peptide-modified lipids, one may cite lipids that are bonded with sugars, antibodies, or peptides that are compatible with the target cells or target tissue. By using modified lipids, the liposome can be actively transmitted to the target cells or target tissue.

There are no particular limitations on the mixing amount (mole fraction) of functional lipids and modified lipids used when preparing the liposome, but 0 to 50% of the entirety of liposome membrane constituent lipids is preferable, 0 to 30% is more preferable, and 0 to 20% is even more preferable.

[Liposome]

As mentioned above, liposome is a microscopic closed vesicle having an internal phase enclosed by a lipid bilayer.

Ideally, with respect to the liposome, it is preferable that: a) the liposome has a barrier function that prevents cyclodextrin from leaking from the liposome internal phase to the external phase after substituting or diluting the external phase of the liposome preparatory liquid; b) the liposome has membrane permeability that allows permeation of the active compound in the step of introducing the active compound from the liposome external phase to the internal phase, in combination with a barrier function that prevents cyclodextrin from leaking to the external phase; and c) the liposome has a barrier function that prevents all of a complex of the active compound and cyclodextrin (also referred to as an "active compound/cyclodextrin complex") and free (uncomplexed) active compounds and cyclodextrin, if any, from leaking to the external phase once the active compound is entrapped in the internal phase. In the case where it is used as a medicine, it is preferable that the liposome exhibits in vivo stability and has a barrier function that prevents all of the active compound/cyclodextrin complex and free active compounds and cyclodextrin, if any, from leaking to the liposome external phase in blood when the liposome is administered in vivo.

The composition of membrane constituents for liposome having such membrane permeability at a level allowing practical application can be appropriately selected by those skilled in the art according to the active compound, cyclodextrin, target tissue and the like by referencing as necessary the embodiments described below (Hiroshi Kikuchi, et al., "Liposome I—Preparation Method and Assay Method—," Cell Technology (1983), 2(9): pp. 1136-1149, and reference literature cited in said literature).

The permeability of the liposome membrane toward a substance largely depends on the molecular weight of the substance, as in biomembranes, and the permeability is generally considered to largely differ with a molecular weight around 1000 as a threshold. By chance, among stable cyclodextrins, the smallest cyclodextrin α-cyclodextrin has a molecular weight of 973; β-cyclodextrin has a molecular weight of 1135; γ-cyclodextrin has a molecular weight of 1297; and hydroxypropyl-β-cyclodextrin (HP-β-cyclodextrin) has a molecular weight of 1380 to 1480. Thus, the liposomes exhibit low membrane permeability toward the cyclodextrins. Therefore, the membrane constituents, etc. are appropriately set according to the cyclodextrin, whereby the cyclodextrin, once entrapped in the liposome internal phase, can be prevented sufficiently from leaking to the liposome external phase even if membrane fluidity is enhanced, for example, by raising a temperature as described later. On the other hand, the membrane constituents, etc. are appropriately set according to the active compound, whereby the liposome membrane becomes permeable to the active compound. The active compound, when incorporated in the liposome internal phase, forms a complex (generally having a molecular weight much larger than 1000) with cyclodextrin, exceedingly reducing the liposome membrane permeability.

Without being bound by theory, not only does the cyclodextrin have the property having sufficiently low liposome membrane permeability in itself as such, but also the cyclodextrin has the property of enhancing its solubility (nominal solubility) by forming a complex with the active compound and further has the property of reducing liposome membrane permeability toward the active compound by forming a complex with the active compound. By chance, these properties of the cyclodextrin are ideal for the entrapment and retention of the active compound by the liposome according to the present invention.

When used as a medicine, it is preferable that the active compound/cyclodextrin complex be released from the liposome after the liposome reaches the target tissue, cells, or intracellular organelles. With respect to the liposome, the membrane constituents themselves are ordinarily biodegradable, and ultimately decompose in target tissue or the like. It is thought that the entrapped active compound/cyclodextrin complex (and free active compounds, if any) is released in this manner. Finally, it is thought that the active compound/cyclodextrin complex releases free active compounds through dilution effect, chemical equilibrium, or enzymatic cyclodextrin degradation. Moreover, it is also acceptable if the liposome itself is incorporated into cells.

Not only can the liposome composition be targeted to target tissue such as solid cancer, but it can also be used to transmit active compounds to hematological cancer and so on. It can also be used as a slow release formulation, controlled release formulation, etc. in blood.

The particle size of liposome can be set according to the objective. For example, when it is intended to transmit liposome to cancerous tissue or inflamed tissue by the EPR (Enhanced Permeability and Retention) effect as an injection product or the like, it is preferable that liposome particle size be 30 to 400 nm, and it is more preferable that the particle size be 50 to 200 nm. In the case where the intention is to transmit liposome to macrophage, it is preferable that liposome particle size be 30 to 1000 nm, and it is more preferable that the particle size be 100 to 400 nm. In the case where liposome composition is to be used as an oral preparation or transdermal preparation, the particle size of liposome can be set at several microns. It should be noted that (1) in normal tissue, vascular walls serve as barriers (because the vascular walls are densely constituted by vascular endothelial cells), and microparticles such as supermolecules and liposome of specified size cannot be distributed within the tissue. However, in diseased tissue, vascular walls are loose (because interstices exist between vascular endothelial cells), increasing vascular permeability, and supermolecules and microparticles can be distributed to extravascular tissue (enhanced permeability). Moreover, (2) the lymphatic system is well developed in normal tissue, but it is known that the lymphatic system is not developed in diseased tissue, and that supermolecules or microparticles, once incorporated, are not recycled through the general system, and are retained in the diseased tissue (enhanced retention)—this is called the EPR effect (Matsumura, Maeda, Cancer Research, (1986), 46: pp. 6387-6392). Consequently, it is possible to control pharmacokinetics by adjusting liposome particle size.

In the present invention, liposome particle size means the weight-average particle size according to the dynamic light scattering method (quasi-elastic light scattering method). Here, particle size is shown that is measured by dynamic light scattering instruments (e.g., Zetasizer Nano ZS model manufactured by Malvern Instruments Ltd. and ELS-8000 manufactured by Otsuka Electronics Co., Ltd.). The instruments measure Brownian motion of the particles, and particle size is determined based on established dynamic light scattering methodological theory.

There are no particular limitations on the solvent of the liposome internal phase, and one may cite, for example, buffer solutions such as phosphate buffer solution, citrate buffer solution, and phosphate-buffered physiological saline solution, physiological saline water, culture mediums for cell culturing, etc. In the case where buffer solution is used as solvent, it is preferable that the concentration of buffer agent be 5 to 300 mM, and 10 to 100 mM is more preferable. There are no particular limitations on the pH of the liposome internal phase, but 3 to 11 is preferable, and 4 to 9 is more preferable.

[Liposome Composition]

A liposome composition is offered according to the present invention. The liposome composition contains liposome, and further contains cyclodextrin and an active compound in the liposome internal phase. As mentioned above, the liposome composition includes both a solid form and a liquid form. In the case where the liposome composition is in a solid form, it can be made into a liquid form by dissolving or suspending it in a prescribed solvent as described below. In the case where the liposome composition is frozen solid, it can be made into a liquid form by melting by leaving it standing at room temperature.

The concentration of liposome and the concentration of the active compound in the liposome composition can be appropriately set according to the liposome composition objective, formulation, etc. In the case where the liposome composition is a liquid formulation, the concentration of liposome as the concentration of all lipids constituting the liposome may be set at 0.2 to 100 mM, and preferably at 1 to 30 mM. The concentration (dosage) of active compound in the case where the liposome composition is used as a medicine is described below. With respect to the quantity of cyclodextrin in the liposome composition, it is preferable that it be 0.1 to 1000 mol equivalent relative to the active compound, and it is more preferable that it be 1 to 100 mol equivalent relative to the active compound.

In the liposome of the present invention, an active compound and cyclodextrin may be apportioned to the lipid bilayer.

There are no particular limitations on the solvent (dispersion medium) of the liposome composition in the case where the liposome composition is a liquid formulation, and one may cite, for example, buffer solutions such as phosphate buffer solution, citrate buffer solution, and phosphate-buffered physiological saline solution, physiological saline water, and culture mediums for cell culturing. There are no particular limitations on the pH of the liposome external phase of the liposome composition, but 3 to 11 is preferable, and 4 to 9 is more preferable.

One may also add the following to the liposome composition: sugar, such as monosaccharides such as glucose, galactose, mannose, fructose, inositol, ribose, and xylose; disaccharides such as lactose, sucrose, cellobiose, trehalose, and maltose; trisaccharides such as raffinose and melezitose; polysaccharides such as cyclodextrin; and sugar alcohols such as erythritol, xylitol, sorbitol, mannitol and maltitol;

polyvalent alcohols such as glycerin, diglycerin, polyglycerin, propylene glycol, polypropylene glycol, ethylene glycol, diethylene glycol, triethylene glycol, polyethylene glycol, ethylene glycol monoalkylether, diethylene glycol monoalkylether, 1,3-butylene glycol. One may also use combinations of sugar and alcohol.

For purposes of stable long-term storage of the liposome that is dispersed in the solvent (dispersion medium), from the standpoint of physical stability including coagulation and so on, it is preferable to eliminate the electrolyte in the solvent (dispersion medium) as much as possible. Moreover, from the standpoint of chemical stability of the lipids, it is preferable to set the pH of the solvent (dispersion medium) from acidic to the vicinity of neutral (pH 3.0 to 8.0), and to remove dissolved oxygen through nitrogen bubbling.

There are no particular limitations on the concentration of the sugar or polyvalent alcohol contained in the liposome composition, but in a state where the liposome is dispersed in a solvent, for example, it is preferable that the concentration of sugar be 2 to 20% (W/V), and 5 to 10% (W/V) is more preferable. With respect to the concentration of polyvalent alcohol, 1 to 5% (W/V) is preferable, and 2 to 2.5% (W/V) is more preferable. These solvents can also be used as the liposome external phase in the liposome dispersion liquid, and by substituting or diluting the liposome external phase of the liposome preparatory solution with these solvents, it is possible to change the solutions of the liposome external phase into these solutions.

It is preferable that solid formulations of the liposome composition include, for example, sugar, such as monosaccharides such as glucose, galactose, mannose, fructose, inositole, ribose, and xylose; disaccharides such as lactose, sucrose, cellobiose, trehalose, and maltose; trisaccharides such as raffinose and melezitose; polysaccharides such as cyclodextrine; and sugar alcohols such as erythritol, xylitol, sorbitol, mannitol, and maltitol. More preferable are blends of glucose, lactose, sucrose, trehalose, and sorbitol. Even more preferable are blends of lactose, sucrose, and trehalose. By this means, solid formulations can be stably stored over long periods. When frozen, it is preferable that solid formulations contain polyvalent alcohols (aqueous solutions) such as glycerin, diglycerin, polyglycerin, propylene glycol, polypropylene glycol, ethylene glycol, diethylene glycol, triethylene glycol, polyethylene glycol, ethylene glycol monoalkylether, diethylene glycol monoalkylether and 1,3-butylene glycol. With respect to polyvalent alcohols (aqueous solutions), glycerin, propylene glycol, and polyethylene glycol are preferable, and glycerin and propylene glycol are more preferable. By this means, it is possible to stably store the solid formulation over long periods. Sugars and polyvalent alcohols may be used in combination.

[Method of Manufacture of Liposome Composition]

According to the present invention, a manufacturing method is provided for the manufacture of a liposome composition. The method for manufacturing the liposome composition includes: a step in which a liposome dispersion liquid that contains liposome and that further contains cyclodextrin in the liposome internal phase is provided; a step in which the aforementioned liposome dispersion liquid is mixed with the active compound; and a step in which the aforementioned active compound is introduced into the liposome internal phase of the aforementioned liposome dispersion liquid.

It is preferable that the step in which a liposome dispersion liquid is provided includes a step in which a liposome preparatory solution is provided, and a step in which the liposome external phase of the aforementioned liposome preparatory solution is substituted or diluted so as to adjust the concentration of the cyclodextrin in the liposome external phase.

The liposome preparatory liquid can be prepared by preparing the liposome in a cyclodextrin solution. There are no particular limitations on the cyclodextrin solution, so long as the solution contains the cyclodextrin.

A higher cyclodextrin concentration in the cyclodextrin solution is more preferable. The cyclodextrin concentration can be set according to the solubility of cyclodextrin in a solvent (described later), viscosity, etc. A higher cyclodextrin concentration in the liposome internal phase of the liposome dispersion liquid can be achieved in this manner, whereby a larger amount of the active compound can be entrapped. For example, the cyclodextrin solution can have a cyclodextrin concentration of 100 to 250 mM, preferably 100 to 200 mM.

As the solvent in the cyclodextrin solution, one may cite, for example, buffer solutions such as phosphate buffer solutions, citrate buffer solutions, and phosphate-buffered physiological saline solutions, physiological saline water, culture media for cell culturing, etc. The pH of the cyclodextrin solution can be set appropriately and is not particularly limited. pH 3 to 11 is preferable, pH 4 to 9 is more preferable, and pH 5 to 8 is even more preferable.

The cyclodextrin solution can be obtained by mixing cyclodextrin with the solvent such that the cyclodextrin is dissolved therein. If necessary, the cyclodextrin solution can also be obtained more rapidly, for example, by heating the solvent to approximately 50° C. and dissolving cyclodextrin therein.

With respect to liposome preparation, one may cite the lipid film method (Vortex method), reverse phase evaporation method, ultrasonic method, pre-vesicle method, ethanol injection method, French press method, cholic acid removal method, Triton X-100 batch method, $Ca^{2+}$ fusion method, ether injection method, annealing method, freeze-thaw method, etc.

The various conditions (quantities of membrane constituents, temperature, etc.) in liposome preparation may be suitably selected according to the liposome preparation method, target liposome composition, particle size, etc. (see op. cit, Kikuchi (1983), etc.). However, cyclodextrin is known to have the effect of removing lipid (particularly, cholesterol, etc.) from liposomes. It is therefore preferable that the amount of lipid used in the liposome preparation be set in consideration of this effect.

The liposome particle size may be optionally adjusted as necessary. Particle size may be adjusted, for example, by conducting extrusion (extrusion filtration) under high pressure using a membrane filter of regular pore diameter. Particle size adjustment may be conducted at any timing during manufacture of the liposome composition of the present invention. For example, it may be conducted before adjustment of the liposome external phase in the liposome preparatory solution, after adjustment of the liposome external phase in the liposome preparatory solution, or after introduction of the active compound into the liposome internal phase. It is preferable to conduct the particle size adjustment before introducing the active compound into the liposome internal phase, and it is more preferable to conduct it before adjusting the liposome external phase in the liposome preparatory solution.

The liposome dispersion liquid can be obtained by substituting or diluting the liposome external phase of the obtained liposome preparatory solution so as to adjust the concentration of the cyclodextrin in the liposome external phase. The substitution or dilution of the liposome external phase may be conducted once, or a combination of various types of substitution or dilution methods may be conducted multiple times.

As a method for substituting the liposome external phase of the liposome preparatory solution, one may cite dialysis, centrifugal separation, and gel filtration.

Dialysis may be conducted, for example, using a dialysis membrane. As a dialysis membrane, one may cite a membrane with molecular weight cut-off such as a cellulose tube or Spectra/Por.

With respect to centrifugal separation, centrifugal acceleration may be conducted preferably at 100,000 g or higher, and more preferably at 300,000 g or higher. By substituting the liposome external phase by centrifugation, one may also conduct liposome concentration in conjunction with substitution of the liposome external phase.

Gel filtration may be carried out, for example, by conducting fractionation based on molecular weight using a column such as Sephadex or Sepharose.

As a method for diluting the liposome external phase of the liposome preparatory liquid, one may cite, for example, a method which involves adding a cyclodextrin-free solution to the liposome external phase.

As the solvent (dispersion medium) used when substituting and/or diluting the liposome external phase, one may cite, for example, buffer solutions such as phosphate buffer solution, citrate buffer solution, and phosphate-buffered physiological saline solution, physiological saline water, and culture medium for cell culturing. There are no particular limitations on the pH of said solvent, but 3 to 11 is preferable, 4 to 10 is more preferable, and 5 to 10 is even more preferable. As described below, a pH gradient may be used to introduce the active compound into the liposome internal phase. In this case, the pH of the solvent may be set so that the liposome external phase attains the target pH.

It is more preferable that the obtained liposome dispersion liquid not substantially contain cyclodextrin in the liposome external phase. This allows the active compound to be introduced into the liposome internal phase more effectively.

However, the active compound may be introduced into the liposome internal phase even in the case where cyclodextrin has for some reason been added to the liposome external phase of the liposome dispersion liquid, and even when the liposome external phase of the liposome dispersion liquid contains cyclodextrin. In this case as well, it is preferable that the liposome dispersion liquid contain a higher concentration of cyclodextrin in the liposome internal phase than in the liposome external phase. Particularly, ½ or lower of the cyclodextrin concentration in the liposome internal phase is preferable, and ⅕ or lower thereof is more preferable based on the cyclodextrin concentration of the liposome external phase, At one's option as necessary, it is possible to use a pH gradient in introducing the active compound into the liposome internal phase. In this case, the liposome internal and external phases in the liposome dispersion liquid differ in pH by preferably 1 to 5, more preferably 2 to 3. Either the liposome internal or external phase can have the higher pH according to the type of the active compound. On the other hand, it is also acceptable if the liposome internal and external phases do not substantially have difference in pH, i.e., the liposome external and internal phases have substantially the same pH. The pH gradient can be adjusted by using a compound conventionally known in the art used in pH gradient methods. One may cite, for example, amino acids such as arginine, histidine, and glycine; acids such as ascorbic acid, benzoic acid, citric acid, glutamic acid, phosphoric acid, acetic acid, propionic acid, tartaric acid, carbonic acid, lactic acid, boric acid, maleic acid, fumaric acid, malic acid, adipic acid, hydrochloric acid, and sulfuric acid; salts of the aforementioned acids such as sodium salt, potassium salt, and ammonium salt; and alkaline compounds such as tris-hydroxymethylamino methane, ammonia water, sodium hydride, and potassium hydride, etc.

Moreover, at one's option as necessary, it is possible to use an ammonium sulfate ion gradient or the like in introducing the active compound into the liposome internal phase. In this case, a larger difference in ion concentration between the liposome internal and external phases in the liposome dispersion liquid is more preferable, and it is desirable that the difference be preferably 10 mM or more, more preferably 20 mM or more, even more preferably 50 mM or more.

There are no limitations on the ions used in the ion gradient method, and one may cite ammonium sulfate, ammonium chloride, ammonium borate, ammonium formate, ammonium acetate, ammonium citrate, ammonium tartrate, ammonium succinate, ammonium phosphate, etc. Moreover, with respect to the ion gradient method, the ion concentration of the liposome internal phase can be selected appropriately according to the type of the active compound. A higher ion concentration is more preferable and is preferably 10 mM or higher, more preferably 20 mM or higher, even more preferably 50 mM or higher. Either the liposome internal or external phase can have the higher ion concentration according to the type of the active compound. On the other hand, it is also acceptable if the liposome internal and external phases do not substantially have difference in ion concentration, i.e., the liposome external and internal phases have substantially the same ion concentration. The ion gradient may be adjusted by substituting or diluting the liposome external phase.

With respect to the lipid concentration of liposome in the liposome dispersion liquid, 1 to 100 mM is preferable, and 1 to 50 mM is more preferable. Within these ranges, it is possible to suitably form a greater number of liposome particles without impairing the physical properties of the liposome dispersion liquid.

The liposome composition can be obtained by mixing the obtained liposome dispersion liquid and the active compound, and by introducing the active compound into the liposome internal phase of the liposome dispersion liquid. It is preferable that the step of introduction include a step in which the membrane permeability of the liposome is enhanced in the mixed solution of liposome dispersion liquid and the active compound. By this means, entrapment of the active compound in the liposome can be accomplished in a shorter period of time. However, even if no particular operations are conducted for the purpose of enhancing the membrane permeability of the liposome after mixing of the liposome dispersion liquid and the active compound, it is possible to entrap the active compound in the liposome if the required time is taken.

In the step in which the active compound is mixed, it is possible to use a substance dissolved in a solvent or a solid substance as the active compound according to the physical properties of the active compound. There are no particular limitations on the solvent, and one may use, for example, a substance identical to the liposome external phase of the liposome dispersion liquid. Moreover, the active compound may be mixed with the liposome dispersion liquid by adding a solution of the active compound thereto. The amount of the active compound that is mixed therewith is preferably 0.001 to 10 mol equivalents, more preferably 0.01 to 1 mol equivalent, relative to the amount of cyclodextrin in the liposome dispersion liquid.

As a method of enhancing the membrane permeability of liposome in the obtained mixed solution, one may cite the method of heating the mixed solution, the method of adding a membrane fluidizer to the mixed solution, etc.

In the case where the mixed solution is heated, the active compound can generally be more efficiently introduced into the liposome internal phase by heating to higher temperatures. Specifically, it is preferable to set the temperature of heating taking into consideration the thermal stability of the active compound and the employed liposome membrane constituents. In particular, it is preferable that the temperature of heating be set to the phase transition temperature of the lipid bilayer membrane of the liposome or higher. Moreover, in the step of introducing the active compound into the liposome internal phase, there are no particular limitations on the heating temperature. For example, 5° C. or higher is preferable, and room temperature, for example, 20° C. or higher is more preferable. Also, it is preferable that the heating temperature be set to a temperature equal to or higher than the phase transition temperature. However, the present invention is not limited to these heating temperatures by any means.

The "phase transition temperature" of the lipid bilayer membrane of liposome means the temperature at which heat absorption starts (the temperature when endothermic reaction begins) in differential thermal analysis of elevated temperatures conditions. Differential thermal analysis is a technique enabling analysis of the thermal properties of specimens by measuring the temperature difference between a specimen and reference substance as a function of time or temperature while changing the temperature of the specimen and reference substance. In the case where differential thermal analysis is conducted with respect to liposome membrane constituents, the liposome membrane components fluidize as temperature increases, and endothermic reaction is observed. As is widely known in this technical field, the temperature range in which endothermic reaction is observed greatly varies according to the liposome membrane components. For example, in the case where liposome membrane components consist of a pure lipid, the temperature range in which endothermic reaction is observed is extremely narrow, and endothermic reaction is often observed within a range of ±1° C. relative to the endothermic peak temperature. On the other hand, in the case where liposome membrane components consist of multiple lipids, and particularly in the case where liposome membrane components consist of lipids derived from natural materials, the temperature range in which endothermic reaction is observed tends to widen, and endothermic reaction is observed, for example, within a range of ±5° C. relative to the endothermic peak temperature (that is, a broad peak is observed). According to the present invention, it is thought that liposome membrane fluidization is increased, and membrane permeability of the active compound is increased by raising the temperature higher than the phase transition temperature of the liposome lipid bilayer membrane.

For example, although dependent on the thermal stability and so on of the active compound and the employed liposome membrane constituents, it is preferable to have a temperature range from the phase transition temperature of the liposome lipid bilayer membrane to +20° C. of the phase transition temperature; a temperature range from the phase transition temperature to +10° C. of the phase transition temperature is more preferable; and a temperature range from +5° C. of the phase transition temperature to +10° C. of the phase transition temperature is even more preferable.

In general, the heating temperature is ordinarily 20 to 100° C.; 40 to 80° C. is preferable; and 45 to 65° C. is more preferable, and it is preferable that the heating temperature is higher than or equal to the phase transition temperature.

Specifically, in the case of a liposome membrane whose principal ingredients are dipalmitoyl phosphatidylcholine (phase transition temperature as simple substance: 41° C.) and cholesterol, although it also depends on the composition thereof, a heating temperature of 40 to 60° C. is ordinarily preferable, and 45 to 50° C. is more preferable. Moreover, in the case of a liposome membrane whose principal ingredients are hydrogenated soy phosphatidylcholine (HSPC; phase transition temperature as simple substance: 50 to 60° C.) and cholesterol, although it also depends on the composition thereof, a heating temperature of 50 to 70° C. is ordinarily preferable, and 55 to 65° C. is more preferable. However, these heating temperatures in no way limit the present invention.

In the heating step, there are no particular limitations on the time during which the temperature is maintained at or above the phase transition temperature, and this may be properly set within a range, for example, of several seconds to 30 minutes. Taking into consideration the thermal stability of the active compound and lipids as well as efficient mass production, it is desirable to conduct the treatment within a short time. That is, it is preferable that the elevated temperature maintenance period be 1 to 30 minutes, and 2 minutes to 5 minutes is more preferable. However, these temperature maintenance times in no way limit the present invention.

Moreover, as stated above, it is also possible to enhance liposome membrane permeability by adding a membrane fluidizer to the obtained mixed solution (that is, adding it to the external phase side of the liposome). As a membrane fluidizer, one may cite organic solvents, surfactants, enzymes, etc. that are soluble in aqueous solvents. More specifically, as organic solvents, one may cite, for example, monovalent alcohols such as ethyl alcohol and benzyl alcohol; polyvalent alcohols such as glycerin and propylene glycol; aprotic polar solvents such as dimethyl sulfoxide (DMSO). As surfactants, one may cite, for example, anionic surfactants such as fatty acid sodium, monoalkyl sulfate, and monoalkyl phosphate; cationic surfactants such as alkyl trimethyl ammonium salt; ampholytic surfactants such as alkyl dimethylamine oxide; and non-ionic surfactants such as polyoxyethylene alkylether, alkyl monoglyceryl ether, and fatty acid sorbitan ester. As enzymes, one may cite, for example, cholinesterase and cholesterol oxidase. Those skilled in the art may set the quantity of membrane fluidizer according to the composition of liposome membrane constituents, the membrane fluidizer, etc., and taking into consideration the degree of efficiency of entrapment of the active compound due to addition of the membrane fluidizer, the stability of the liposome, etc.

Without being bound by theory, according to the present invention, it is thought that the active compound added to the liposome external phase moves spontaneously to the liposome internal phase based on a mechanism shown below by entrapping in advance cyclodextrin in the liposome internal phase. That is, under conditions that allow the active compound to have higher solubility in the liposome internal phase than the solubility in the liposome external phase, i.e., to be energetically more stable in the liposome internal phase than in the liposome external phase, it is considered that the active compound capable of penetrating the liposome membrane penetrates the liposome membrane against the concentration gradient of the active compound such that it moves from the liposome external phase to the liposome internal phase. As described above, it is considered that the active compound, once moving to the liposome internal phase, forms a complex with cyclodextrin, thereby cannot penetrate to the liposome external phase, and thus is retained in the liposome internal phase.

As described above, cyclodextrin has previously been known to have the effect of removing lipid (particularly, cholesterol) from biomembranes or liposome membranes. For example, it has been reported that red blood cells are hemolyzed by cyclodextrin. Therefore, it seems that the idea of entrapping in advance cyclodextrin in the liposome internal phase for preparing liposomes was difficult to produce.

The manufacturing method of the liposome composition of the present invention may further include a step of adjusting the liposome external phase of the obtained liposome composition and/or a step of drying the obtained liposome composition after the above-mentioned introduction step.

That is, when using a liposome composition as a liquid formulation, the liposome composition in a liquid form obtained in the above-mentioned introduction step may be used without modification as the final liposome composition, or the liposome external phase in the liquid liposome composition obtained in the above-mentioned introduction step may be adjusted (replaced, etc.) to make a final liposome composition. When doing so, the adjustment of the liposome external phase may be carried out similarly to the adjustment of the liposome external phase in a liposome preparatory liquid. In the case where the liposome composition is a liquid formulation, it may be used without further modification.

Furthermore, in the case where the liposome composition is to be made into a solid preparation, the liquid liposome composition obtained in the above-mentioned introduction step may be dried to make the final solid liposome composition. Freeze drying and spray drying may be cited as examples of methods for drying the liposome composition. In cases where the liposome composition is a solid preparation, it may be dissolved or suspended in a suitable solvent and used as a liquid formulation. The solvent to use may be appropriately set according to the purpose of use, etc. for the liposome composition, and in the case of using the liposome composition as an injection product, for example, the solvent is preferably sterile distilled water. In the case of using the liposome composition as a medicine, the physician or patient may inject the solvent into a vial into which the solid preparation is entrapped, for example, to make the preparation at the time of use. In the case where the liquid liposome composition is a frozen solid preparation, it may be stored in a frozen state, and put in use as a liquid formulation by returning it to a liquid state by leaving it to melt at room temperature or by rapidly melting it with heat at the time of use.

[Pharmaceutical Compositions, Etc.]

The liposome composition of the present invention may be used as a pharmaceutical composition such as a curative medicine and a diagnostic drug in the medical field. For example, the liposome composition can be used as a curative medicine by using an antitumor agent as the active compound and can be used as a diagnostic drug by using a contrast agent as the active compound. The liposome composition may also be used as a cosmetic product or a food additive.

In the case where the liposome composition of the present invention is used as a pharmaceutical composition, the liposome composition may be administered by injection (intravenous, intra-arterial, or local injection), orally, nasally, subcutaneously, pulmonarily, or through eye drops, and in particular local injection to a targeted group of cells or organ or other such injection is preferable in addition to intravenous injection, subcutaneous injection, intracutaneous injection, and intra-arterial injection. Tablet, powder, granulation, syrup, capsule, liquid, and the like may be given as examples of the formulation of the liposome composition in the case of oral administration. Injection product, drip infusion, eye drop, ointment, suppository, suspension, cataplasm, lotion, aerosol, plaster, and the like may be given as examples of formulations of the liposome composition in the case of non-oral administration, and an injection product and drip infusion agent are particularly preferable.

The dosage of the pharmaceutical composition differs markedly depending on the type of target disease, the type of the active compound, as well as the age, sex, and weight of the patient, the severity of the symptoms, along with other factors, but ordinarily, the daily dosage for adults is about 0.1 to 2000 mg, and optionally preferably 1 to 100 mg, and the administration may be divided into more than one dose per day.

When the liposome composition is used as a cosmetic product, as the form of the cosmetic product, one may cite, for example, lotions, creams, toners, moisturizers, foams, foundations, lipsticks, face packs, skin washes, shampoos, rinses, conditioners, hair tonics, hair liquids, hair creams, etc.

[Kit]

According to the present invention, a kit is provided for preparing the liposome composition. The kit may be used to prepare the liposome composition as a medicine, which may be used by a physician in clinical setting or a patient.

The kit includes a liposome reagent. The liposome reagent may be either a solid or a liquid form. If the liposome reagent is in a liquid form, the above-mentioned liposome dispersion liquid may be used as the liposome reagent. Also, if the liposome reagent is in a solid form, the liposome reagent can be dissolved or suspended in an appropriate solvent to obtain the liposome dispersion liquid, and the above-mentioned liposome dispersion liquid can be dried to obtain the liposome reagent. Drying may be carried out similarly to the above-mentioned drying of the liposome composition. When using the kit, if the liposome reagent is in a solid form, the liposome regent can be dissolved or suspended in an appropriate solvent to make the liposome dispersion liquid. When doing so, the solvent is similar to the liposome external phase in the above-mentioned liposome dispersion liquid.

The kit of the present invention preferably further contains an active compound. The active compound may be either in a solid or liquid form (a state of dissolved or suspended in a solvent). When using the kit, if the active compound is in a solid form, it is preferable that it be dissolved or suspended in an appropriate solvent to make a liquid form. The solvent can be appropriately set according to the physical properties and the like of the active compound, and may be made similar to the liposome external phase in the above-mentioned liposome dispersion liquid, for example.

In the kit, the liposome reagent and the active compound may be packaged separately, or they may be in solid forms and mixed together.

In the case where the liposome reagent is in a solid form, excluding cases of dissolving or suspending to form a liposome dispersion liquid as above, the kit may be used by carrying out a step similar to that of mixing the liposome dispersion liquid and the active compound and of introducing the active compound in the liposome internal phase of the liposome dispersion liquid in the manufacturing method of the above-mentioned liposome composition. It is thereby possible to manufacture a liposome composition in which an active compound is introduced into the liposome internal phase of the liposome reagent.

In the case where the liposome reagent and the active compound are both in solid forms and are packaged together, the mixture of the liposome reagent and the active compound is appropriately dissolved or suspended in a solvent. When doing so, the solvent is similar to the liposome external phase in the above-mentioned liposome dispersion liquid. It is thereby possible to form a state in which the liposome dispersion liquid and the active compound are mixed, after which use is made possible by carrying out other steps in the introduction of the active compound in the liposome internal phase of the liposome dispersion liquid in the manufacturing method of the above-mentioned liposome composition.

Embodiments

The present invention is specifically described by giving embodiments and comparative examples, but is not limited to the embodiments below.

[Embodiment 1]

<Preparation of an Aqueous Solution for the Liposome Internal Phase>

840.6 mg of citric acid monohydrate was dissolved in pure water, and this was diluted to 20 mL to prepare 200 mM aqueous citric acid. After dissolving 280 mg or 560 mg of HP-β-cyclodextrin (manufactured by ROQUETTE) in 1 mL of 200 mM aqueous citric acid and adjusting the solution with aqueous ammonia to a pH of 5.5, the aqueous solution for the liposome internal phase was diluted to 2 mL with pure water.

An aqueous solution for the liposome internal phase free from HP-β-cyclodextrin was prepared by adjusting 1 mL of 200 mM aqueous citric acid with aqueous ammonia to a pH of 5.5 and then diluting the aqueous solution for the liposome internal phase to 2 mL with pure water (Table 1).

<Preparation of the Liposome Preparatory Liquid>

After dissolving 44.4 mg of hydrogenated soybean phosphatidylcholine (manufactured by Lipoid), 14.5 mg of cholesterol (manufactured by Sigma), and 17.4 mg of polyethylene glycol 2000-phosphatidylethanolamine (manufactured by Genzyme, MPEG 2000-distearoyl phosphatidylethanolamine) in 3 mL of chloroform, the chloroform was removed under reduced pressure in a rotary evaporator to create a lipid film. 2 mL of the aqueous solution for the liposome internal phase with various compositions described in Table 1 below was heated to approximately 60° C. and added to the obtained lipid film, and this was agitated to prepare a liposome preparatory liquid. After treating the liposome preparatory liquid with ultrasonic waves for 20 minutes, it was granulated with an extruder (manufactured by Lipex Biomembranes) heated to approximately 65° C. to obtain the granulated liposome preparatory liquid. The particle size of the liposomes in the obtained liposome preparatory liquid was measured using a dynamic light scattering method, and all were 90 to 100 nm.

<Preparation of the Liposome Dispersion Liquid>

Using Sephadex G-50 columns, the obtained liposome preparatory liquid was eluted with 0.9% sodium chloride/10 mM histidine aqueous solution (pH=7.6), substituting the liposome external phase with the 0.9% sodium chloride/10 mM histidine aqueous solution. After substituting the liposome external phase, this was centrifuged for 30 minutes at 400,000×g. After centrifuging, this was redispersed, and 0.9% sodium chloride/10 mM histidine aqueous solution was used to prepare a volume of 2 mL, obtaining the liposome dispersion liquid.

<Preparation of the Active Compound Solution>

An ethanol solution (50 mg/mL) of E7107 ((8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide) was diluted 500 times with 0.9% sodium chloride/10 mM histidine aqueous solution to obtain 0.1 mg/mL of E7107 solution.

<Preparation of the Liposome Composition>

0.1 mL of the liposome dispersion liquid and 1 mL of the E7107 solution were mixed in a 10-mL glass vessel, and this was incubated for 3 minutes in 55° C. water to obtain a liposome composition with E7107 introduced in the liposomes.

<Measurement of the Entrapment Ratio>

The entrapment ratio was determined as described below.

The liposome composition entrapping an active compound was ultracentrifuged for 30 minutes at 400,000×g. The active compound concentration in the filtrate was measured with HPLC, quantitating the amount of active compound not entrapped in the liposomes. The entrapment ratio was calculated using the formula below.

$$\text{Entrapment ratio (\%)} = \frac{\text{Qty. of active compound in total qty. (mg)} - \text{Qty. of active compound in filtrate after ultracentrifugation (mg)}}{\text{Qty. of active compound in total qty. (mg)}} \times 100 \quad \text{[Formula 1]}$$

The results are shown in Table 1. As can be seen from Table 1, the presence of cyclodextrin in the liposome internal water phase achieved entrapment of E7107 with very high efficiency.

TABLE 1

| Composition of aqueous solution for liposome internal phase | Entrapment ratio (%) |
|---|---|
| 0 mM HP-beta-CyD, 100 mM citric acid, pH = 5.5 | 75.9 |
| 100 mM HP-beta-CyD, 100 mM citric acid, pH = 5.5 | 98.4 |
| 200 mM HP-beta-CyD, 100 mM citric acid, pH = 5.5 | 99.4 |

<Stability in Rat Blood Plasma>

The E7107 entrapped liposome after ultracentrifugation was resuspended so as to be 0.1 mL, and this was mixed with 1 mL of rat blood plasma. The amount of E7107 within the liposome was measured immediately, at 24 hours, 48 hours, and 72 hours, after mixing by a method described below. The time-dependent stability of the active compound entrapment ratio was evaluated.

The liposome and E7107 leaked out to the liposome external phase were separated using PD-10 Column (manufactured by GE Healthcare). The collected liposome fraction and 10% Tween 80 solution were mixed at a 9:1 ratio to disrupt the liposome, and the amount of E7107 retained within the liposome was quantified by HPLC.

The residual rate within the liposome was measured by dividing the amount of E7107 at 24 hours, 48 hours, or 72 hours after mixing by the amount of E7107 immediately after mixing.

The measurement results are shown in FIG. 1. The presence of cyclodextrin in the liposome internal phase dramatically improved stability in the blood plasma. In FIG. 1, HP-β-CD means HP-β-cyclodextrin.

[Embodiment 2]
<Preparation of the Liposome Composition>

Similarly to Embodiment 1, the liposome dispersion liquid was obtained in which the composition of the aqueous solution for the liposome internal phase was 250 mM HP-β-cyclodextrin/100 mM citric acid (pH=5.5) and the liposome external phase was substituted with 0.9% sodium chloride/10 mM histidine aqueous solution (pH=7.6).

Subsequently, the liposome dispersion liquid and the E7107 solution were mixed in a 10-mL glass vessel, and this was incubated for 1 minute, 5 minutes, 1 hour, or 6 hours in 5° C., 20° C., 40° C., 50° C., or 60° C. water to obtain a liposome composition.

The measurement results of the entrapment ratio are shown in Table 2. As can be seen from Table 2, heating during the entrapment operation of E7107 achieved reduction in entrapment operation time. Also, it was demonstrated that E7107 is gradually entrapped even at room temperature (20° C.).

TABLE 2

| Temperature | Operation time | Entrapment ratio (%) |
|---|---|---|
| 60° C. | 1 minute | 99.2 |
|  | 5 minutes | 99.4 |
| 50° C. | 1 minute | 56.8 |
|  | 5 minutes | 99.4 |
| 40° C. | 1 minute | 4.1 |
|  | 5 minutes | 87.5 |
|  | 1 hour | 99.4 |
| 20° C. | 1 minute | 0 |
|  | 5 minutes | 0 |
|  | 1 hour | 13.1 |
|  | 6 hours | 49.6 |
| 5° C. | 5 minutes | 0 |
|  | 1 hour | 0 |
|  | 6 hours | 0 |

[Embodiment 3]
<Preparation of an Aqueous Solution for the Liposome Internal Phase>

396.4 mg of ammonium sulfate and 189.1 mg of citric acid monohydrate were dissolved in pure water, and this was diluted to 15 mL to prepare 200 mM ammonium sulfate/60 mM aqueous citric acid. After dissolving 700 mg of HP-β-cyclodextrin or 790 mg of HP-γ-cyclodextrin (manufactured by Sigma) in 2.5 mL of 200 mM ammonium sulfate/60 mM aqueous citric acid and adjusting the solution with aqueous ammonia to a pH of 5.5, the aqueous solution for the liposome internal phase was diluted to 5 mL with pure water.

An aqueous solution for the liposome internal phase free from cyclodextrin was prepared by adjusting 2.5 mL of 200 mM ammonium sulfate/60 mM aqueous citric acid with aqueous ammonia to a pH of 5.5 and then diluting the aqueous solution for the liposome internal phase to 5 mL with pure water (Table 3).

<Preparation of the Liposome Preparatory Liquid>

After dissolving 317.9 mg of hydrogenated soybean phosphatidylcholine, 116.0 mg of cholesterol, and 130.4 mg of polyethylene glycol 2000-phosphatidylethanolamine in 10 mL of chloroform, this was accurately dispensed into three vials, after which the chloroform of one vial was removed under reduced pressure in a rotary evaporator to create a lipid film. 5 mL of the aqueous solution for the liposome internal phase with various compositions described in Table 3 below was heated to approximately 60° C. and added to the obtained lipid film, and this was agitated to prepare a liposome preparatory liquid. After treating the liposome preparatory liquid with ultrasonic waves for 20 minutes, it was granulated with an extruder (manufactured by Lipex Biomembranes) heated to approximately 65° C. to obtain the liposome preparatory liquid. The particle size of the liposomes in the obtained liposome preparatory liquid was measured using a dynamic light scattering method, and all were 90 to 100 nm.

<Preparation of the Liposome Dispersion Liquid>

Similarly to Embodiment 1, 5 mL of the liposome dispersion liquid was obtained.

<Preparation of the Active Compound Solution>

The eribulin mesylate was dissolved in 0.9% sodium chloride/10 mM histidine aqueous solution to obtain 1 mg/mL eribulin mesylate solution.

<Preparation of the Liposome Composition>

0.5 mL of the liposome dispersion liquid and 0.5 mL of the eribulin mesylate solution were mixed in a 10-mL glass vessel, and this was incubated for 3 minutes in 55° C. water to obtain a liposome composition with eribulin mesylate introduced in the liposomes.

<Measurement of the Entrapment Ratio>

The entrapment ratio was determined similarly to Embodiment 1. The results are shown in Table 3. As can be seen from Table 3, the presence of cyclodextrin in the liposome internal water phase achieved entrapment of eribulin mesylate with higher efficiency.

TABLE 3

| Composition of aqueous solution for liposome internal phase | Entrapment ratio (%) |
|---|---|
| 0 mM CyD, 100 mM ammonium sulfate, 30 mM citric acid, pH = 5.5 | 90.9 |
| 100 mM HP-beta-CyD, 100 mM ammonium sulfate, 30 mM citric acid, pH = 5.5 | 96.7 |
| 100 mM HP-gamma-CyD, 100 mM ammonium sulfate, 30 mM citric acid, pH = 5.5 | 96.3 |

<Preparation of an Aqueous Solution for the Liposome Internal Phase>

Similarly, 264.3 mg of ammonium sulfate and 126.1 mg of citric acid monohydrate were dissolved in pure water, and a graduated flask was used to dilute this to 10 mL to prepare 200 mM ammonium sulfate/60 mM aqueous citric acid. 560 mg of HP-β-cyclodextrin, 632 mg of HP-γ-cyclodextrin, 584 mg of $G_2$-β-cyclodextrin (manufactured by ENSUIKO Sugar Refining Co., Ltd.), and 432 mg of CAPTISOL (manufactured by CyDex Pharmaceutical, Inc.) were weighed, and each was dissolved in 1 mL of 200 mM ammonium sulfate/60 mM aqueous citric acid. After adjusting this with aqueous ammonia to a pH of 5.5, this was diluted with pure water to 2 mL to prepare the aqueous solution for the liposome internal phase.

An aqueous solution for the liposome internal phase free from cyclodextrin was prepared by adjusting 1 mL of 200 mM ammonium sulfate/60 mM aqueous citric acid with aqueous ammonia to a pH of 5.5 and then diluting the aqueous solution for the liposome internal phase to 2 mL with pure water (Table 4).

TABLE 4

| Number | Buffer | CyD | pH |
|---|---|---|---|
| 1 | 100 mM ammonium sulfate/ 30 mM citric acid | — | 5.5 |
| 2 | 100 mM ammonium sulfate/ 30 mM citric acid | 200 mM HP-beta-CyD | 5.5 |
| 3 | 100 mM ammonium sulfate/ 30 mM citric acid | 200 mM HP-gamma-CyD | 5.5 |
| 4 | 100 mM ammonium sulfate/ 30 mM citric acid | 200 mM $G_2$-beta-CyD | 5.5 |
| 5 | 100 mM ammonium sulfate/ 30 mM citric acid | 100 mM Captisol | 5.5 |

<Preparation of the Liposome Preparatory Liquid>

80 mg each of a lipid mixture (hydrogenated soybean phosphatidylcholine:cholesterol:polyethylene glycol 2000-phosphatidylethanolamine=58.6:19.2:22.2 (by weight)) was weighed, 2 mL of the aqueous solution for the liposome internal phase with various compositions described in Table 4 below was heated to approximately 80° C. and added thereto, and this was agitated to prepare the liposome preparatory liquid. This liposome preparatory liquid was granulated using an extruder (manufactured by Lipex Biomembranes) heated to approximately 80° C. to obtain the liposome preparatory liquid.

<Preparation of the Liposome Dispersion Liquid>

The obtained liposome preparatory liquid was diluted to 10 mL with the 0.9% sodium chloride/10 mM histidine aqueous solution (pH=7.6), and this was centrifuged for 30 minutes at 400,000×g. After centrifuging, all of the filtrate was disposed. The precipitate was redispersed with the 0.9% sodium chloride/10 mM histidine aqueous solution, and a graduated flask was used to prepare 1 mL of liquid, obtaining the liposome dispersion liquid.

<Preparation of the Drug Solution>

Eribulin mesylate was dissolved in the 0.9% sodium chloride/10 mM histidine aqueous solution and 5 mg/mL eribulin mesylate solution was obtained.

<Preparation of the Liposome Composition>

0.96 mL of the liposome dispersion liquid and 0.24 mL of the eribulin mesylate solution were mixed in a 10-mL glass vessel, and this was incubated for 3 minutes in 60° C. water to obtain a liposome composition with eribulin mesylate introduced in the liposomes.

<Stability in Rat Blood Plasma>

0.2 mL of the prepared eribulin mesylate entrapped liposome and 1.8 mL of rat blood plasma were mixed, and this was shaken at 37° C. using a liquid phase incubator. Immediately after the mixing of the liposome composition and rat blood plasma, sampling was performed at 6 hours, 12 hours, 24 hours, 48 hours and 120 hours after the shaking was begun, and free body fraction was separated by gel filtration column. The obtained free body fraction of eribulin mesylate was measured with HPLC as quantity of eribulin mesylate which has leaked from the liposomes.

The measurement results are shown in FIG. 2. As can be seen in FIG. 2, it was indicated that the eribulin mesylate was stably retained in the blood plasma even over the long time span of 120 hours, and gradual release was possible. Moreover, it was indicated that particularly the liposome containing cyclodextrin in the internal phase can more stably retain eribulin mesylate for a long period.

[Embodiment 4]

<Preparation of the Liposome Composition>

Similarly to Embodiment 3, the liposome dispersion liquid was obtained in which the composition of the aqueous solution for the liposome internal phase was 200 mM cyclodextrin/100 mM ammonium sulfate/30 mM citric acid (pH=7.0) and the liposome external phase was substituted with 0.9% sodium chloride/10 mM histidine aqueous solution (pH=7.6).

Subsequently, the liposome dispersion liquid and the eribulin mesylate solution were mixed in a 10-mL glass vessel, and this was incubated for 1 minute, 5 minutes, 1 hour, or 6 hours in 5° C., 20° C., 40° C., 50° C., or 60° C. water to obtain a liposome composition.

<Measurement of the Entrapment Ratio>

The measurement results of the entrapment ratio are shown in Table 5. As can be seen from Table 5, heating during the entrapment operation of eribulin mesylate achieved reduction in entrapment operation time. Also, it was demonstrated that eribulin mesylate is gradually entrapped even at room temperature (20° C.).

TABLE 5

| Temperature | Operation time | Entrapment ratio (%) |
|---|---|---|
| 60° C. | 1 minute | 84.5 |
|  | 5 minutes | 94.4 |
| 50° C. | 1 minute | 13.7 |
|  | 5 minutes | 94.0 |
| 40° C. | 1 minute | 4.5 |
|  | 5 minutes | 24.3 |
|  | 1 hour | 76.0 |
| 20° C. | 1 minute | 4.4 |
|  | 5 minutes | 4.1 |
|  | 1 hour | 7.9 |
|  | 6 hours | 10.4 |
| 5° C. | 5 minutes | 4.8 |
|  | 1 hour | 7.4 |
|  | 6 hours | 4.2 |

[Embodiment 5]

<Preparation of an Aqueous Solution for the Liposome Internal Phase>

1.46 g of glutamine was dissolved in pure water, and this was diluted to 100 mL to prepare 100 mM glutamine aqueous solution. The pH was measured, and it was 5.2. Moreover, 28.0 g of HP-β-cyclodextrin and 1.46 g of glutamine were dissolved in pure water, and this was diluted to 100 mL to prepare 200 mM HP-β-cyclodextrin/100 mM glutamine aqueous solution. 31.6 g of HP-γ-cyclodextrin and 1.46 g of glutamine were dissolved in pure water, and this was diluted to 100 mL to prepare 200 mM HP-γ-cyclodextrin/100 mM glutamine aqueous solution. 29.2 g of $G_2$-β-cyclodextrin and 1.46 g of glutamine were dissolved in pure water, and this was diluted to 100 mL to prepare 200 mM $G_2$-β-cyclodextrin/100 mM glutamine aqueous solution. 43.2 g of CAPTISOL and 1.46 g of glutamine were dissolved in pure water, and this was diluted to 100 mL to prepare 200 mM CAPTISOL/100 mM glutamine aqueous solution. These glutamine aqueous solutions containing each cyclodextrin were adjusted with hydrochloric acid and sodium hydroxide to a pH of 5.2 (Table 6).

Similarly, 1.55 g of histidine was dissolved in pure water, and this was diluted to 100 mL to prepare 100 mM histidine aqueous solution (pH=7.6). Moreover, 200 mM HP-β-cyclodextrin/100 mM histidine aqueous solution, 200 mM HP-γ-cyclodextrin/100 mM histidine aqueous solution, 200 mM $G_2$-β-cyclodextrin/100 mM histidine aqueous solution, and 200 mM CAPTISOL/100 mM histidine aqueous solution were prepared. These histidine aqueous solutions containing each cyclodextrin were adjusted with hydrochloric acid and sodium hydroxide to a pH of 7.6 (Table 6).

Moreover, similarly, 1.74 g of arginine was dissolved in pure water, and this was diluted to 100 mL to prepare 100 mM arginine aqueous solution (pH=11.1). Moreover, 200 mM HP-β-cyclodextrin/100 mM arginine aqueous solution, 200 mM HP-γ-cyclodextrin/100 mM arginine aqueous solution, 200 mM G$_2$-β-cyclodextrin/100 mM arginine aqueous solution, and 200 mM CAPTISOL/100 mM arginine aqueous solution were prepared. These arginine aqueous solutions containing each cyclodextrin were adjusted with hydrochloric acid and sodium hydroxide to a pH of 11.1 (Table 6).

<Preparation of the Liposome Preparatory Liquid>

200 mg each of a lipid mixture (hydrogenated soybean phosphatidylcholine: cholesterol:polyethylene glycol 2000-phosphatidylethanolamine=58.6:19.2:22.2 (by weight)) was weighed, 5 mL of the aqueous solution for the liposome internal phase with various compositions described in Table 6 below was heated to approximately 80° C. and added thereto, and this was agitated to prepare the liposome preparatory liquid. After treating the liposome preparatory liquid with ultrasonic waves for 20 minutes, it was granulated with an extruder (manufactured by Lipex Biomembranes) heated to approximately 80° C. to obtain the granulated liposome preparatory liquid. The particle size of the liposomes in the obtained liposome preparatory liquid was measured using a dynamic light scattering method, and all were 90 to 100 nm.

<Preparation of the Liposome Dispersion Liquid>

Using Sephadex G-50 columns, the obtained liposome preparatory liquid was eluted with the aqueous solution for the liposome external phase with various compositions described in Table 6 below, substituting the liposome external phase. After substituting the liposome external phase, this was centrifuged for 30 minutes at 400,000×g. After centrifuging, this was redispersed, and the aqueous solution for the liposome external phase with various compositions described in Table 6 below was used to prepare 5 mL of a liquid, obtaining the liposome dispersion liquid.

<Preparation of the Liposome Composition>

Each of these liposome dispersion liquids and the eribulin mesylate solution prepared similarly to Embodiment 3 were mixed, and this was incubated for 5 minutes in 60° C. water to obtain liposome compositions with eribulin mesylate introduced in the liposomes.

<Measurement of the Entrapment Ratio>

The entrapment ratio was measured similarly to Embodiment 1. The results are shown in Table 6. As can be seen from Table 6, it was demonstrated that even when any cyclodextrin is used in the internal phase, the entrapment ratio of eribulin mesylate is improved.

TABLE 6

| No. | Internal phase Buffer | CyD | External phase (all free from CyD in the external phase) Buffer | Entrapment ratio (%) |
|---|---|---|---|---|
| 1 | 100 mM Glutamine, pH = 5.2 | — | 100 mM Glutamine, pH = 5.2 | 13.2 |
| 2 | | 200 mM HP-β-CyD | | 24.0 |
| 3 | | 200 mM HP-γ-CyD | | 28.9 |
| 4 | | 200 mM G2-β-CyD | | 35.6 |
| 5 | | 200 mM Captisol | | 27.3 |
| 6 | 100 mM Histidine, pH = 7.6 | — | 100 mM Histidine, pH = 7.6 | 20.2 |
| 7 | | 200 mM HP-β-CyD | | 34.1 |
| 8 | | 200 mM HP-γ-CyD | | 31.5 |
| 9 | | 200 mM G2-β-CyD | | 39.5 |
| 10 | | 200 mM Captisol | | 29.8 |
| 11 | 100 mM Arginine, pH = 11.1 | — | 100 mM Arginine, pH = 11.1 | 2.3 |
| 12 | | 200 mM HP-β-CyD | | 29.1 |
| 13 | | 200 mM HP-γ-CyD | | 13.6 |
| 14 | | 200 mM G2-β-CyD | | 20.4 |
| 15 | | 200 mM Captisol | | 10.6 |

[Embodiment 6]

<Preparation of the Liposome Composition>

Similarly to Embodiment 5, the liposome dispersion liquid was obtained (Table 7).

The doxorubicin was dissolved in 100 mM glutamine aqueous solution (pH=5.2) or 100 mM histidine aqueous solution (pH=7.6) to obtain 1 mg/mL doxorubicin aqueous solution.

0.1 mL of the liposome dispersion liquid and 0.1 mL of the doxorubicin aqueous solution were mixed in a 10-mL glass vessel, and this was incubated for 5 minutes in 60° C. water.

<Measurement of the Entrapment Ratio>

The entrapment ratio was measured similarly to Embodiment 1. The results are shown in Table 7. As can be seen from Table 7, the presence of cyclodextrin in the liposome internal phase improved the entrapment ratio of doxorubicin.

TABLE 7

| No. | Internal phase Buffer | CyD | External phase (all free from CyD in the external phase) Buffer | Entrapment ratio (%) |
|---|---|---|---|---|
| 1 | 100 mM Glutamine, pH = 5.2 | — | | 74.9 |
| 2 | | 200 mM HP-β-CyD | 100 mM Glutamine, | 87.5 |

TABLE 7-continued

| | Internal phase | | External phase (all free from CyD in the external phase) | Entrapment |
|---|---|---|---|---|
| No. | Buffer | CyD | Buffer | ratio (%) |
| 3 | | 200 mM HP-γ-CyD | pH = 5.2 | 81.6 |
| 4 | | 200 mM G2-β-CyD | | 81.2 |
| 5 | | — | | 82.6 |
| 6 | 100 mM Histidine, | 200 mM HP-β-CyD | 100 mM Histidine, | 93.7 |
| 7 | pH = 7.6 | 200 mM HP-γ-CyD | pH = 7.6 | 84.3 |
| 8 | | 200 mM G2-β-CyD | | 91.7 |

[Embodiment 7]
<Preparation of the Liposome Dispersion Liquid>

Similarly to Embodiment 5, the liposome dispersion liquids were obtained in which the liposome internal phase was 100 mM glutamine aqueous solution, 200 mM HP-β-cyclodextrin/100 mM glutamine aqueous solution, 200 mM HP-γ-cyclodextrin/100 mM glutamine aqueous solution, or 200 mM $G_2$-β-cyclodextrin/100 mM glutamine aqueous solution, and the external phase was 100 mM glutamine aqueous solution (Table 8).

Moreover, the liposome dispersion liquids were obtained in which the liposome internal phase was 100 mM histidine aqueous solution, 200 mM HP-β-cyclodextrin/100 mM histidine aqueous solution, 200 mM HP-γ-cyclodextrin/100 mM histidine aqueous solution, or 200 mM $G_2$-β-cyclodextrin/100 mM histidine aqueous solution, and the external phase was 100 mM histidine aqueous solution (Table 8).

<Preparation of the Active Compound Solution>

The paclitaxel was dissolved in 5 mM HP-β-cyclodextrin/100 mM glutamine aqueous solution (pH=5.2) or 5 mM HP-β-cyclodextrin/100 mM histidine aqueous solution (pH=7.6) to obtain 4 μg/mL paclitaxel aqueous solution.

<Preparation of the Liposome Composition>

5.3 mg of HP-β-cyclodextrin was dissolved in 0.75 mL of the liposome dispersion liquid in a 10-mL glass vessel, substituting the liposome external phase liquid with 5 mM HP-β-cyclodextrin. This was mixed with 0.25 mL of the paclitaxel aqueous solution, and this was incubated for 5 minutes in 60° C. water to obtain a liposome composition.

<Measurement of the Entrapment Ratio>

The liposome composition immediately after entrapment was diluted to 2 mL with 5 mM HP-β-cyclodextrin. Of this, 1 mL was used, and the paclitaxel concentration and the hydrogenated soybean phosphatidylcholine (HSPC) concentration were measured with HPLC. Moreover, the remaining 1 mL was diluted to 10 mL with pure water, and this was centrifuged for 40 minutes at 400,000×g. The filtrate was completely removed, and the obtained precipitate was resuspended with pure water so as to be 10 mL. Again, this was centrifuged for 40 minutes at 400,000×g. The filtrate was completely removed, and the obtained precipitate was resuspended with pure water so as to be 1 mL. The paclitaxel concentration and the HSPC concentration in the obtained liposome composition were measured with HPLC. The entrapment ratio was determined using the formula below.

$$\text{Entrapment ratio (\%)} = \frac{\text{Qty. of paclitaxel before centrifugation (mg)}}{\text{Qty. of HSPC before centrifugation (mg)}} \div \frac{\text{Qty. of paclitaxel after centrifugation (mg)}}{\text{Qty. of HSPC after centrifugation (mg)}} \times 100 \quad \text{[Formula 2]}$$

The results are shown in Table 8. As can be seen from Table 8, when the cyclodextrins of the same species were allowed to exist in the liposome internal and external phases, respectively, the entrapment ratio of paclitaxel was significantly improved by setting the cyclodextrin concentration in the internal phase to a higher concentration. Even when the cyclodextrins of different species were allowed to exist in the liposome internal and external phases, respectively, the entrapment ratio of paclitaxel was also significantly improved by setting the cyclodextrin concentration in the internal phase to a higher concentration.

TABLE 8

| | Internal phase | | External phase (all containing 5 mM HP-β-CyD in the external phase) | | Entrapment |
|---|---|---|---|---|---|
| No. | Buffer | CyD | Buffer | CyD | ratio (%) |
| 1 | 100 mM Glutamine, | — | 100 mM Glutamine, | 5 mM HP-β-CyD | 29.7 |
| 2 | pH = 5.2 | 200 mM HP-β-CyD | pH = 5.2 | | 45.1 |
| 3 | | 200 mM HP-γ-CyD | | | 39.0 |
| 4 | | 200 mM G2-β-CyD | | | 41.8 |
| 5 | | 200 mM Captisol | | | 35.0 |
| 6 | 100 mM Histidine, | — | 100 mM Histidine, | | 26.0 |
| 7 | pH = 7.6 | 200 mM HP-β-CyD | pH = 7.6 | | 44.7 |
| 8 | | 200 mM HP-γ-CyD | | | 41.6 |
| 9 | | 200 mM G2-β-CyD | | | 46.0 |
| 10 | | 200 mM Captisol | | | 31.0 |

[Embodiment 8]

Similarly to Embodiment 1, an aqueous solution for the liposome internal phase in which the composition was 250 mM HP-β-cyclodextrin and 100 mM citric acid was used to obtain a liposome composition (E7107 concentration: 0.2 mg/mL, total lipid concentration: 10 μmol/mL).

Moreover, non-formulated E7107 was prepared by dissolving E7107 in a physiological saline solution (OTSUKA PHARMACEUTICAL CO., LTD.) containing 5% DMSO/ 5% Tween 80 (E7107 concentration: 3 mg/mL).

WiDr (obtained from Dainippon Sumitomo Pharma Co., Ltd.), which is a human colon cancer cell line, was cultured and grown in a 10% bovine fetal serum-containing RPMI1640 culture. The cells were separated from the flask using 0.05% Trypsin-EDTA solution and collected. After washing with PBS, the cells were suspended in Hank's Balanced Salt Solution (manufactured by GIBCO) so as to be $5 \times 10^7$ cells/mL and kept on ice. 100 µL of cell suspension liquid was subcutaneously injected in the right ventral portion of 6- to 8-week old female nude mice (BALB/cAJcl-nu/nu; CLEA Japan, Inc.). Each mouse was observed daily, and notes were made appropriately in cases where abnormal conditions were found. Calipers were used to measure the tumor size over time, and the tumor size was calculated based on the calculation formula: major axis×(minor axis squared)÷2. Moreover, the mouse body weight was also measured over time. At the point when the tumor size was 100 to 200 mm$^3$, the mice were separated into groups such that the average values of the tumor sizes and the mouse body weights were uniform among the test groups. The prepared liposome composition (1 mg/kg) or the non-formulated E7107 (30 mg/kg) was administered in a single dose into the caudal veins of the cancer-bearing mice, and blood and tumor tissue were taken over time after administration. The obtained blood was centrifuged at 4° C. to separate blood plasma. With regard to the tumor tissue, a physiological saline solution was added approximately 4 times the quantity of the tumor tissue to prepare a uniform homogenate. A mixed solution of acetonitrile (Wako Pure Chemical Industries, Ltd.) and methanol (Wako Pure Chemical Industries, Ltd.) in equal quantities containing 0.2 mL of an internal standard substance (propranolol (manufactured by Sigma), 100 ng/mL) was added to the obtained blood plasma (0.05 mL) and tumor homogenate (0.05 g), and this was mixed. Proteins were removed by centrifugation, and the obtained filtrate was filtered through Multi-Screen Filter plate (manufactured by Millipore). Then, the filtrate (5 µL) was analyzed with high-performance liquid chromatography (HPLC)/mass spectrometer (LC/MS/MS) shown below to measure the E7107 concentration in the blood plasma and the tumor.

Changes in the E7107 concentration in the blood plasma and the tumor tissue when administered in a single dose into the veins of the cancer-bearing mice are shown in FIG. 3. As can be seen from FIG. 3, it was demonstrated that the retention of E7107 in the blood plasma and the tumor is significantly improved by preparing the liposomal formulation of E7107.

[Embodiment 9]

Similarly to Embodiment 1, an aqueous solution for the liposome internal phase in which the composition was 250 mM HP-β-cyclodextrin and 100 mM citric acid was used to obtain a liposome dispersion liquid. The mixing ratio between the liposome dispersion liquid and the E7107 solution was variously changed to obtain 5 kinds of liposome compositions (E7107 concentration: 0.2 mg/mL, total lipid concentration: 2.5 µmol/mL; E7107 concentration: 0.2 mg/mL, total lipid concentration: 5 µmol/mL; E7107 concentration: 0.2 mg/mL, total lipid concentration: 10 µmol/mL; E7107 concentration: 0.2 mg/mL, total lipid concentration: 20 µmol/mL; E7107 concentration: 0.2 mg/mL, total lipid concentration: 40 µmol/mL). Similarly to Embodiment 1, the entrapment ratios of liposome compositions were measured, and all were 95% or more.

Cancer-bearing mice were prepared by subcutaneously injecting WiDr (obtained from Dainippon Sumitomo Pharma Co., Ltd.), which is a human colon cancer-derived cell, in the ventral portion of female nude mice (BALB/cAJcl-nu/nu). The prepared various liposomal formulations of E7107 were administered in a single dose into the caudal veins of the cancer-bearing mice, and blood was taken at 24 hours and 72 hours after administration. The obtained blood was centrifuged at 4° C. to separate blood plasma. Similarly to Embodiment 8, the E7107 concentration in the blood plasma was measured.

Changes in the E7107 concentration in the blood plasma and the tumor tissue when administered in a single dose into the veins of the cancer-bearing mice are shown in FIG. 4. As can be seen from FIG. 4, every liposome composition exhibited similar changes in the E7107 concentration in the blood plasma and the tumor.

[Embodiment 10]

WiDr (obtained from Dainippon Sumitomo Pharma Co., Ltd.), which is a human colon cancer cell line, was cultured and grown in a 10% bovine fetal serum-containing RPMI1640 culture. The cells were separated from the flask using 0.05% Trypsin-EDTA solution and collected. After washing with PBS, the cells were suspended in Hank's Balanced Salt Solution (manufactured by GIBCO) so as to be $5 \times 10^7$ cells/mL and kept on ice. 100 µL of cell suspension liquid was subcutaneously injected in the right ventral portion of 6- to 8-week old nude mice (CLEA Japan, Inc.). Each mouse was observed daily, and notes were made appropriately in cases where abnormal conditions were found. Calipers were used to measure the tumor size over time, and the tumor size was calculated based on the calculation formula: major axis×(minor axis squared)÷2. Moreover, the mouse body weight was also measured over time. At the point when the tumor size was 100 to 200 mm$^3$, the mice were separated into groups such that the average values of the tumor sizes and the mouse body weights were uniform among the test groups (five mice per test group). E7107 (200 µL/20 g) was administered in a single dose into the caudal veins of the cancer-bearing mice.

As a solution administered to the E7107-2.5 mg/kg group (group 2), a DMSO solution, a Tween-80 solution, and 5% glucose solution were added at a 3.5:6.5:90 ratio to E7107 to adjust the E7107 concentration to 0.25 mg/mL.

The E7107 entrapped liposome compositions used in the groups 3 and 4 were prepared similarly to Embodiment 1, and the E7107 concentration was adjusted to 0.25 mg/mL.

The tumor size, the ratio to control, and the average body weight are shown in Table 9 as therapeutic effect on tumor growth 5 days after administration.

TABLE 9

| Group | Administered solution | Tumor (mm$^3$) | Ratio to control | Body weight (g) |
| --- | --- | --- | --- | --- |
| 1 | Control | 352.22 | 100 | 21.78 |
| 2 | E7107-2.5 mg/kg | 204.34 | 56 | 20.32 |
| 3 | Liposome E7107-2.5 mg/kg | 150.28 | 40 | 19.98 |
| 4 | Liposome E7107(130 mM HP-beta-CyD)-2.5 mg/kg | 102.08 | 28 | 20.52 |

The tumor-growth suppression effect and the body weight loss 5 days after administration were statistically analyzed by a parametric method. When a P value of less than 0.05 is shown in each comparison between the test groups, this means statistically significant difference. The tumor-growth suppression effect of each administration group exhibited a value of less than 0.05 relative to the control group. No significant increase was observed in antitumor effect of the liposome E7107-2.5 mg/kg group, compared with the E7107-2.5 mg/kg group (P=0.22). However, the liposome E7107 (130 mM HP-β-cyclodextrin)-2.5 mg/kg group containing the HP-β-cyclodextrin exhibited significant increase in tumor reduction, compared with the E7107-2.5 mg/kg group (P=0.018).

With regard to the body weight loss, no significant decrease was seen in any comparison between the groups.

From these results, there are no particular limitations on the dose of E7107 per day, and usually, the antitumor effect of E7107 can be exerted by administering the liposome composition to a human so as to be 1 to 100 mg.

[Embodiment 11]
<Preparation of the Aqueous Solution for the Liposome Internal Phase>

Similarly to Embodiment 1, 100 mM ammonium sulfate/30 mM aqueous citric acid (pH=5.5) and 200 mM HP-β-cyclodextrin/100 mM ammonium sulfate/30 mM aqueous citric acid (pH=5.5) were prepared.

<Preparation of the Liposome Preparatory Liquid>

Hydrogenated soybean phosphatidylcholine, cholesterol, and polyethylene glycol 2000-phosphatidylethanolamine were weighed according to the quantities shown in Table 10. After dissolving each in 3 mL of chloroform, the chloroform was removed under reduced pressure in a rotary evaporator to create a lipid film. 10 mL of the prepared aqueous solution for the liposome internal phase (100 mM ammonium sulfate/30 mM aqueous citric acid for Rp. 1 to 4 and 200 mM HP-β-cyclodextrin/100 mM ammonium sulfate/30 mM aqueous citric acid for Rp. 5 to 8) was heated to approximately 80° C. and added to the obtained lipid film, and this was agitated to prepare a liposome preparatory liquid. This was granulated using an extruder (manufactured by Lipex Biomembranes) heated to approximately 80° C. to obtain the granulated liposome preparatory liquid. The particle size of the liposomes in the obtained liposome preparatory liquid was measured using a dynamic light scattering method, and Rp. 1 was 77 nm, Rp. 2 95 nm, Rp. 3 79 nm, Rp. 4 128 nm, Rp. 5 81 nm, Rp. 6 122 nm, Rp. 7 76 nm, and Rp. 8 110 nm.

TABLE 10

| Rp. | Hydrogenated soybean phosphatidylcholine | Cholesterol | Polyethylene glycol 2000-phosphatidylethanolamine |
|---|---|---|---|
| 1 | 234 mg | 76 mg | 15 mg |
| 2 | 234 mg | 76 mg | 15 mg |
| 3 | 222 mg | 73 mg | 87 mg |
| 4 | 222 mg | 73 mg | 87 mg |
| 5 | 234 mg | 76 mg | 15 mg |
| 6 | 234 mg | 76 mg | 15 mg |
| 7 | 222 mg | 73 mg | 87 mg |
| 8 | 222 mg | 73 mg | 87 mg |

<Preparation of the Liposome Composition>

Similarly to Embodiment 1, the liposome dispersion liquid was obtained. Also, eribulin mesylate was dissolved in 0.9% sodium chloride/10 mM histidine aqueous solution, and 5 mg/mL eribulin mesylate solution was obtained.

4.8 mL of each of the liposome dispersion liquids and 0.6 mL of eribulin mesylate solution were mixed in 10-mL glass vessels, which were incubated for 3 minutes in 60° C. water to obtain liposome compositions with eribulin mesylate introduced in the liposomes. 24.6 mL of the 0.9% sodium chloride/10 mM histidine aqueous solution was added to each of the liposome compositions, and a 0.2-μm polyvinylidene fluoride (PVDF) filter (GD/X filter manufactured by Whatman plc.) was used for filtering and sterilization, obtaining an administration sample (eribulin mesylate concentration: 0.1 mg/mL).

Similarly to Embodiment 1, the entrapment ratio was measured and confirmed to be at least 90% in each of the prescriptions.

Female nude mice (NU/NU, Charles River Laboratories Japan, Inc.) were subcutaneously inoculated with human melanoma LOX cells, and 11 or 12 days later, the samples were administered into the caudal veins so as to be 10 mL/kg (1.0 mg/kg for the eribulin mesylate). A blood sample was taken and tumor tissue extraction was carried out with a cardiac puncture at fixed periods after administration (15 minutes, 30 minutes, 1, 2, 4, 8, 12, 24, 36, and 48 hours) (n=3). The blood was sampled in a test tube containing heparin, and within 30 minutes of the sampling, the blood was separated by centrifuging at 1,500×g for 10 minutes at 4° C. to obtain the blood plasma. All of the tumor tissue was extracted, washed with PBS, and wiped with water-absorbent paper, and then the tissue weight was immediately weighed. The tissue was placed in a test tube and cooled in ice water, and then stored at −80° C. until analysis was carried out.

The eribulin mesylate in the blood plasma and in the tumor tissue was measured using LC/MS/MS.

The PK parameters were calculated using non-compartment model analysis software (WinNonlin version 5.0.1). The results of the blood plasma PK parameters and tumor tissue PK parameters of the eribulin mesylate are shown respectively in Table 11 and Table 12.

TABLE 11

Rp. 1-8 and eribulin mesylate blood plasma PK parameters in LOX cancer-bearing mice

| Prescription | $AUC_{0-t}$ (ng · hr/mL) | $AUC_{0-\infty}$ (ng · hr/mL) | CL (mL/hr/kg) | $V_{ss}$ (mL/kg) | $t_{1/2}$ (hr) | MRT (hr) | Ratio 1 |
|---|---|---|---|---|---|---|---|
| Rp. 1 | 253049 | 258274 | 3.87 | 43.99 | 8.7 | 11.4 | 707.1 |
| Rp. 2 | 176148 | 177893 | 5.62 | 56.40 | 6.8 | 10.0 | 487.0 |
| Rp. 3 | 228151 | 233067 | 4.29 | 48.93 | 8.4 | 11.4 | 638.1 |
| Rp. 4 | 221494 | 230541 | 4.34 | 55.88 | 9.4 | 12.9 | 631.2 |
| Rp. 5 | 279946 | 286266 | 3.49 | 42.02 | 8.5 | 12.0 | 783.8 |
| Rp. 6 | 254737 | 256681 | 3.90 | 33.46 | 4.9 | 8.6 | 702.8 |
| Rp. 7 | 445934 | 500260 | 2.00 | 41.79 | 14.4 | 20.9 | 1369.6 |
| Rp. 8 | 428899 | 505929 | 1.98 | 47.71 | 16.4 | 24.1 | 1385.2 |
| Eribulin mesylate | 363.02 | 365.247 | 2420 | 8032 | 3.7 | 3.3 | 1.0 |

Ratio 1 = $AUC_{plasma\ liposome}/AUC_{plasma\ eribulin\ mesylate}$

TABLE 12

Rp. 1-8 and eribulin mesylate tumor tissue PK parameters in LOX cancer-bearing mice

| Prescription | $C_{[max]}$ (ng/g) | $t_{[max]}$ (hr) | $AUC_{0-t}$ (ng·hr/mL) | $AUC_{0-\infty}$ (ng·hr/mL) | $t_{1/2}$ (hr) | MRT (hr) | TPI (mL/g) | Ratio 2 |
|---|---|---|---|---|---|---|---|---|
| Rp. 1 | 692.1 | 4.0 | 24960.7 | 34581.8 | 22.8 | 38.8 | 0.13 | 5.5 |
| Rp. 2 | 1002.9 | 8.0 | 16759.6 | 22301.1 | 22.2 | 34.5 | 0.13 | 3.5 |
| Rp. 3 | 3965.7 | 12.0 | 41643.7 | 46297.3 | 16.1 | 23.3 | 0.20 | 7.4 |
| Rp. 4 | 1132.8 | 12.0 | 28377.4 | 45005.6 | 23.7 | 44.3 | 0.20 | 7.2 |
| Rp. 5 | 4076 | 8.0 | 52818.7 | 121915.3 | 49.6 | 76.9 | 0.43 | 19.4 |
| Rp. 6 | 1221.3 | 8.0 | 34559.5 | 57337.7 | 41.1 | 57.1 | 0.22 | 9.1 |
| Rp. 7 | 1394.8 | 8.0 | 47700.7 | 87408.7 | 43.5 | 63.2 | 0.17 | 13.9 |
| Rp. 8 | 1329.2 | 24.0 | 47264.1 | 96661.4 | 39.3 | 65.2 | 0.19 | 15.4 |
| Eribulin mesylate | 323.425 | 0.25 | 4649.521 | 6294.283 | 17.8 | 27.7 | 17.23 | 1.0 |

Ratio 2 = $AUC_{tumor\ liposome}/AUC_{tumor\ eribulin\ mesylate}$

From Table 11 and Table 12, it can be seen that the AUC of the blood plasma and tumor tissue is increased in comparison to the free eribulin mesylate in all liposome compositions Rp. 1 to 8, and therefore, the tumor migration quantity and retention of the eribulin mesylate are improved.

[Embodiment 12]

<Preparation of the Aqueous Solution for the Liposome Internal Phase>

Similarly to Embodiment 3, 200 mM HP-β-cyclodextrin/100 mM ammonium sulfate/30 mM aqueous citric acid (pH=5.5) was prepared.

<Preparation of the Liposome Preparatory Liquid>

221.8 mg of hydrogenated soybean phosphatidylcholine, 72.5 mg of cholesterol, and 86.9 mg of polyethylene glycol 2000-phosphatidylethanolamine were weighted. After dissolving them in 3 mL of chloroform, the chloroform was removed under reduced pressure in a rotary evaporator, and a lipid film was created. 10 mL of the created aqueous solution for the liposome internal phase were heated to approximately 80° C. and added to the obtained lipid film, and this was agitated to prepare a liposome preparatory liquid. This was granulated using an extruder (manufactured by Lipex Biomembranes) heated to approximately 80° C., and a granulated liposome preparatory liquid was obtained. When the particle sizes of the liposomes in the obtained liposome preparatory liquid were measured using a dynamic light scattering method, they were approximately 90 nm.

<Preparation of the Liposome Dispersion Liquid>

Using Sephadex G-50 columns, the obtained liposome preparatory liquid was eluted with 0.9% sodium chloride/10 mM histidine aqueous solution (pH=7.6), substituting the liposome external phase with the 0.9% sodium chloride/10 mM histidine aqueous solution. After substituting the liposome external phase, this was centrifuged for 30 minutes at 400,000×g. After centrifuging, this was redispersed, and the 0.9% sodium chloride/10 mM histidine aqueous solution, was used to prepare 10 mL of liquid, obtaining the liposome dispersion liquid.

<Preparation of the Drug Solution>

Eribulin mesylate was dissolved in the 0.9% sodium chloride/10 mM histidine aqueous solution and 1 mg/mL eribulin mesylate solution was obtained. Also, as administration samples of free bodies, the eribulin mesylate solution was diluted with the 0.9% sodium chloride/10 mM histidine aqueous solution, and a 0.22-μm PVDF filter was used for filtering and sterilizing to obtain administration samples (eribulin mesylate concentrations: 0.1 mg/mL, 0.2 mg/mL and 0.4 mg/mL)

<Preparation of the Liposome Composition>

1.8 mL of the liposome dispersion liquid and 1.2 mL of the eribulin mesylate solution were each mixed in a 10 mL glass vessel, which was incubated for 3 minutes in 60° C. water to obtain a liposome composition with eribulin mesylate introduced in the liposomes. The obtained liposome composition was diluted with the 0.9% sodium chloride/10 mM histidine aqueous solution, and a 0.22 μm PVDF filter was used for filtering and sterilizing to obtain an administration sample (eribulin mesylate concentration: 0.1 mg/mL and 0.2 mg/mL). The entrapment ratio was measured by ultracentrifugation and confirmed to be at least 90%.

WiDr, which is a human colon cancer cell line, was cultured and grown in a 10% bovine fetal serum-containing RPMI1640 culture. The cells were separated from the flask using 0.05% Trypsin-EDTA solution and collected. After washing with PBS, the cells were suspended in Hank's Balanced Salt Solution (manufactured by Gibco BRL Co. Ltd.) so as to be $5\times10^7$ cells/mL and kept on ice. 0.1 mL of cell suspension liquid were subcutaneously injected in the right ventral portion of 7-week old nude mice (Charles River Laboratories Japan, Inc.). Each mouse was observed daily, and notes were made appropriately in cases where abnormal conditions were found. Calipers were used to measure the tumor size over time, and the tumor size was calculated based on the calculation formula: major axis×(minor axis squared)÷2. At the point when the tumor size was 100 to 200 mm³, the mice were separated into groups such that the average values of the tumor sizes and the mouse body weights were uniform among the test groups (five mice per test group), and the drug was administered into the caudal vein (0.2 mL/20 g; 2 times in 7-day intervals).

The measurement results are shown in FIG. 5. As can be seen from FIG. 5, the 1 mg/kg liposome composition administration group exhibited much more excellent antitumor effect than the 2 mg/kg free body administration group or the 4 mg/kg (maximum tolerance dose) free body administration group. Moreover, the tumor completely disappeared from all the individuals in the 1 mg/kg liposome composition administration group and the 2 mg/kg liposome composition administration group. In the 2 mg/kg free body administration group, only 2 out of 5 mice were completely healed, demonstrating increase in the maximum efficacy of liposomal formulation and expansion of the range of this efficacy. Moreover, in this test, deterioration in general conditions was not observed in all the groups.

[Embodiment 13]
<Preparation of the Aqueous Solution for the Liposome Internal Phase Similarly to Embodiment 3, 200 mM HP-β-cyclodextrin/100 mM ammonium sulfate/30 mM aqueous citric acid (pH=5.5) was prepared.
<Preparation of the Drug Solution>

Similarly to Embodiment 12, administration samples (eribulin mesylate concentration: 0.4 mg/mL) of free bodies were obtained.
<Preparation of the Liposome Composition>

Except for the use of the aqueous solution for the liposome internal phase prepared as described above, the liposome composition (eribulin mesylate concentration: 0.3 mg/mL) was obtained similarly to Embodiment 11. Similarly to Embodiment 1, the entrapment ratio was measured and confirmed to be at least 90%.

FaDu (obtained from the American Type Culture Collection), which is a human pharyngeal squamous cell carcinoma line, was cultured and grown in a 10% bovine fetal serum-containing MEM culture. The cells were separated from the flask using 0.05% Trypsin-EDTA solution and collected. After washing with PBS, the cells were suspended in PBS so as to be $5 \times 10^7$ cells/mL and then kept on ice. 0.1 mL of cell suspension liquid were subcutaneously injected in the right ventral portion of 6-week old nude mice (Charles River Laboratories Japan, Inc.). Each mouse was observed daily, and notes made appropriately in cases where abnormal conditions were found. Calipers were used to measure the tumor size over time, and the tumor size was calculated based on the calculation formula: major axis×(minor axis squared)÷2. At the point when the tumor size was 100 to 200 mm³, the mice were separated into groups such that the average values of the tumor sizes and the body weights of mice were uniform among the test groups (five mice per test group), and the drug was administered into the caudal vein (0.2 mL/20 g; 3 times in 7-day intervals).

The results of the change in average tumor volume after sample administration are shown in FIG. 6. As can be seen from FIG. 6, a tumor-reducing effect was not obtained even at 4.0 mg/kg, which is the maximum tolerance dose for free bodies, because the cell line with a low sensitivity to eribulin mesylate was used. Meanwhile, in the 3 mg/kg liposome composition administration group, a clear tumor-reducing effect was found, and the tumor disappeared in all the cases.

[Embodiment 14]
<Preparation of an Aqueous Solution for the Liposome Internal Phase>

Similarly to Embodiment 3, 100 mM ammonium sulfate/30 mM aqueous citric acid (pH=5.5), 200 mM HP-β-cyclodextrin/100 mM ammonium sulfate/30 mM aqueous citric acid (pH=5.5), and 200 mM HP-γ-cyclodextrin/100 mM ammonium sulfate/30 mM aqueous citric acid (pH=5.5) were prepared.
<Preparation of the Drug Solution>

Similarly to Embodiment 12, administration samples (eribulin mesylate concentration: 0.3 mg/mL and 0.4 mg/mL) of free bodies were obtained.
<Preparation of the Liposome Composition>

Except for the use of the aqueous solution for the liposome internal phase prepared as described above, each liposome composition (eribulin mesylate concentration: 0.2 mg/mL) was obtained similarly to Embodiment 11. Similarly to Embodiment 1, the entrapment ratio was measured and confirmed to be at least 90%.

FaDu (obtained from the American Type Culture Collection), which is a human pharyngeal squamous cell carcinoma line, was cultured and grown in a 10% bovine fetal serum-containing MEM culture. The cells were separated from the flask using 0.05% Trypsin-EDTA solution and collected. After washing with PBS, the cells were suspended in PBS so as to be $5 \times 10^7$ cells/mL and kept on ice. 0.1 mL of cell suspension liquid was subcutaneously injected in the right ventral portion of 6-week old nude mice (Charles River Laboratories Japan, Inc.). Each mouse was observed daily, and notes were made appropriately in cases where abnormal conditions were found. Calipers were used to measure the tumor size over time, and the tumor size was calculated based on the calculation formula: major axis×(minor axis squared)÷2. At the point when the tumor size was 100 to 200 mm³, the mice were separated into groups such that the average values of the tumor sizes and the mouse body weights were uniform among the test groups (five mice per test group), and the drug was administered into the caudal vein (0.2 mL/20 g; 3 times in 7-day intervals).

The results of the change in average tumor volume after sample administration are shown in FIG. 7. As can be seen from FIG. 7, a tumor-reducing effect was not obtained even at 4.0 mg/kg, which is the maximum tolerated dose for free bodies, because FaDu is a cell line with a low sensitivity to eribulin mesylate. Meanwhile, a clear tumor-reducing effect was found in the 2 mg/kg liposome composition administration group. Particularly, high effect was confirmed in the liposome composition containing the HP-γ-cyclodextrin in the liposome internal phase such that the tumor completely disappeared in one out of 5 mice.

[Embodiment 15]
<Preparation of an aqueous solution for the liposome internal phase>

Similarly to Embodiment 3, 100 mM ammonium sulfate/30 mM aqueous citric acid (pH=5.5) and 200 mM HP-β-cyclodextrin/100 mM ammonium sulfate/30 mM aqueous citric acid (pH=5.5) were prepared.
<Preparation of the Drug Solution>

Similarly to Embodiment 12, administration samples (eribulin mesylate concentration: 0.2 mg/mL, 0.3 mg/mL, and 0.4 mg/mL) of free bodies were obtained.
<Preparation of the Liposome Composition>

Except for the use of the aqueous solution for the liposome internal phase prepared as described above, each liposome composition (eribulin mesylate concentration: 0.3 mg/mL) was obtained similarly to Embodiment 12. Similarly to Embodiment 1, the entrapment ratio was measured and confirmed to be at least 90%.

ACHN (obtained from the American Type Culture Collection), which is a human renal cancer cell line, was cultured and grown in a 10% bovine fetal serum-containing MEM culture. The cells were separated from the flask using 0.05% Trypsin-EDTA solution and collected. After washing with PBS, the cells were suspended in PBS so as to be $5 \times 10^7$ cells/mL and then kept on ice. 0.1 mL of cell suspension liquid was subcutaneously injected in the right ventral portion of 6-week old nude mice (Charles River Laboratories Japan, Inc.). Each mouse was observed daily, and notes were made appropriately in cases where abnormal conditions were found. Calipers were used to measure the tumor size over time, and the tumor size was calculated based on the calculation formula: major axis×(minor axis squared)÷2. At the point when the tumor size was 150 to 200 mm³, the mice were separated into groups such that the average values of the tumor sizes and the mouse body weights were uniform among the test groups (five mice per test group), and the drug was administered into the caudal vein (0.2 mL/20 g; 3 times in 7-day intervals).

The results of the change in average tumor volume after sample administration are shown in FIG. 8. As can be seen from FIG. 8, because ACHN is a cell line that is resistant to eribulin mesylate, no significant difference was found between any of the 2 mg/kg administration, 3 mg/kg administration, and 4 mg/kg (maximum tolerance dose) free body administration groups and the untreated group 45 days after the start of sample administration. Meanwhile, in the liposome composition 3 mg/kg administration group, a tumor-growth suppression effect was found, and a significant minor tumor volume value was indicated for the untreated group and the free body administration groups 45 days after the start of sample administration. Particularly, the liposome composition containing the HP-β-cyclodextrin in the liposome internal phase exhibited high tumor-growth suppression effect.

From these results, there are no particular limitations on the dose of eribulin mesylate per day, and usually, the antitumor effect of eribulin mesylate can be exerted by administering the liposome composition to a human so as to be 0.1 to 10 mg.

The present application is based on a Japanese patent application (Japanese Patent Application 2009-082521) filed on Mar. 30, 2009, and a U.S. provisional patent application (61/164,653), and a Japanese patent application (Japanese Patent Application 2009-082516) filed on Mar. 30, 2009, and a U.S. provisional patent application (61/164,678), and the contents thereof are incorporated herein as reference.

INDUSTRIAL APPLICABILITY

The present invention is capable of providing a method for manufacturing a liposome with a high retention stability of the active compound with a high entrapment ratio.

The liposome composition of the present invention has industrial applicability in the fields of medicines, cosmetic products and food products. Among them, the liposome composition of the present invention is favorably used in therapeutic applications and diagnostic applications as medicines.

The invention claimed is:

1. A method for preparing a liposome composition, comprising:

(a) preparing a liposome dispersion liquid comprising liposome and further comprising cyclodextrin in both the liposome internal phase and the liposome external phase;
(b) preparing a solution comprising an active compound and/or pharmaceutically acceptable salt thereof;
(c) mixing the liposome dispersion liquid prepared in (a) with the solution prepared in (b), thus preparing a mixed solution that has a higher concentration of cyclodextrin in the liposome internal phase than in the liposome external phase;
(d) heating the mixed solution prepared in (c) to a temperature equal to or higher than the liposome's lipid bilayer phase transition temperature; and
(e) obtaining, from the mixed solution of (d), a liposome composition that comprises the active compound complexed with the cyclodextrin in the liposome internal phase, wherein the liposome in (a) is formed in a cyclodextrin-containing solution;

wherein the cyclodextrin is selected from the group consisting of hydroxypropyl-β-cyclodextrin, hydroxypropyl-γ-cyclodextrin, 6-O-maltosyl-β-cyclodextrin and sufobutylether-β-cyclodextrin; and wherein the liposome's membrane comprises phospholipids that comprise saturated or unsaturated fatty-acid residues with a carbon number of 12 to 20.

2. The method according to claim 1, wherein (a) preparing the liposome dispersion liquid further comprises: substituting or diluting the liposome external phase of the liposome dispersion liquid prepared in (a) with a liposome external phase that is cyclodextrin-free or that results in a liposome dispersion liquid that has a higher concentration of cyclodextrin the liposome internal phase than in the liposome external phase.

3. The method according to claim 1, wherein the temperature equal to or higher than the liposome's lipid bilayer phase transition tempera u is from 20 to 100° C.

4. The method according to claim 1, wherein the temperature equal to or higher than the liposome's lipid bilayer phase transition temperature is from 40 to 80° C.

* * * * *